(12) United States Patent
Yeates et al.

(10) Patent No.: US 7,802,569 B2
(45) Date of Patent: Sep. 28, 2010

(54) AEROSOL PROCESSING AND INHALATION METHOD AND SYSTEM FOR HIGH DOSE RATE AEROSOL DRUG DELIVERY

(75) Inventors: Donovan B. Yeates, Escondido, CA (US); Jinghai Yi, Des Plaines, IL (US); Guanglin Li, Chicago, IL (US)

(73) Assignee: Kaer Biotherapeutics Corporation, San Marcos, CA (US)

( * ) Notice: Subject to any disclaimer, the term of this patent is extended or adjusted under 35 U.S.C. 154(b) by 1063 days.

(21) Appl. No.: 11/315,951

(22) Filed: Dec. 22, 2005

(65) Prior Publication Data

US 2007/0144514 A1 Jun. 28, 2007

(51) Int. Cl.
 *A61M 16/00* (2006.01)
(52) U.S. Cl. .............................. 128/203.12; 128/200.14
(58) Field of Classification Search ............ 128/200.14, 128/200.17, 200.21, 200.22, 200.23, 203.12, 128/203.15, 204.18, 204.25; 239/650
 See application file for complete search history.

(56) References Cited

U.S. PATENT DOCUMENTS

| | | | | |
|---|---|---|---|---|
| 5,522,385 | A * | 6/1996 | Lloyd et al. ............. | 128/203.26 |
| 5,533,406 | A * | 7/1996 | Geise ...................... | 73/863.22 |
| 5,800,598 | A | 9/1998 | Chein et al. | |
| 5,906,202 | A * | 5/1999 | Schuster et al. ........ | 128/203.23 |
| 6,158,431 | A * | 12/2000 | Poole .................... | 128/203.12 |
| 6,367,471 | B1 * | 4/2002 | Genosar et al. ........ | 128/200.23 |
| 7,128,067 | B2 * | 10/2006 | Byron et al. ........... | 128/200.14 |
| 2004/0187869 | A1 * | 9/2004 | Bjorndal et al. ........ | 128/203.15 |
| 2005/0196345 | A1 | 9/2005 | Diederichs et al. | |

FOREIGN PATENT DOCUMENTS

| | | |
|---|---|---|
| GB | 2342874 | 4/2000 |
| WO | 02/21100 | 3/2002 |
| WO | 0221100 | 3/2002 |
| WO | 2005/052288 | 6/2005 |
| WO | 2005052288 | 6/2005 |

OTHER PUBLICATIONS

Kim et al. Multijet and Multistage Aerosol Concentrator: Design and Performance Analysis, Journal of Aerosol Medicine, vol. 14, No. 2, 2001. pp. 245-254.*
Search Report, Written Opinion issued by European Patent Office for EP 06 84 8085.4, dated Mar. 1, 2010 plus the set of claims it refers to.
Extended European Search Report issued by the EPO in EP Application 06848085.4 dated Mar. 10, 2010.

\* cited by examiner

*Primary Examiner*—Quang D Thanh
(74) *Attorney, Agent, or Firm*—Schlee IP International, P.C.; Alexander R. Schlee

(57) ABSTRACT

A method and system is disclosed which is capable of delivering at a high dose rate, respirable solid aerosols derived from aqueous- or nonaqueous-based solutions containing the desired therapeutic agent(s). The method and system comprises the integration of an aerosol generator, an aerosol evaporator, an aerosol concentrator, and an aerosol flow regulator. The aerosol generator generates 10-30 μm droplets, with a narrow size distribution. The aerosol jet is arrested by a coaxial counter-flow heated air jet, and evaporated rapidly by annular swirling heated air. Most of the air, together with the unwanted solvent vapor, is removed from the aerosol stream during the process of aerosol concentration. The output aerosol carries the dry particles to be inhaled by the patient. The respiratory-governed control of aerosol fluid generation system delivers fluid containing the test agent of interest (drug or toxin) to the aerosol generator throughout inhalation.

35 Claims, 13 Drawing Sheets

401　　　　　　　200　　　　　300　　204　405

US 7,802,569 B2

AEROSOL PROCESSING AND INHALATION METHOD AND SYSTEM FOR HIGH DOSE RATE AEROSOL DRUG DELIVERY

FIELD OF THE INVENTION

This invention relates to methods and systems for the processing of aerosols from solvents of high vapor pressure (such as water or alcohol) containing a solute or suspension, and the delivery of solute or suspension as a solid respirable aerosol into the respiratory system. More particularly, it pertains to the delivery of aqueous-based aerosols containing large molecule therapeutic materials such as drugs, biologics, proteins, surfactants and genetic materials to the pulmonary system as respirable dry particle aerosols at a high dose rate.

BACKGROUND OF THE INVENTION

The characteristics of aerosol inhalation patterns for deposition in the respiratory tract, as well as their clearance from the respiratory tract, have been well documented (Yeates, D. B. and Mortensen J. Deposition and Clearance, In: Murray J F. Nadel J A: Textbook of Respiratory Medicine, et 3.Philadelphia, WB Saunders Company, Vol. 1. Chapter 15 pp. 349-384, 2000).

Reduction in Aerosol Inhalation Times

Aerosol drug therapies from liquid solutions, liquid suspensions, and dry powder suspensions have been used in hospitals, outpatient clinics, and at home. Of the new drugs being developed, it has been estimated that 16% will be delivered via the respiratory tract. This includes the treatment of both respiratory and non-respiratory diseases. These new agents include antibiotics, anticancer agents, surfactants, hormones, proteins and peptides. Whereas there are excellent nebulizers for the delivery of microgram quantities of many small molecules, efficient and effective aerosol delivery of many of the above agents presents new challenges for aerosol delivery systems. A result of the limitations of current technology is that, in order to provide a therapeutic level of drug to the pulmonary system, an extended time period for inhalation is required. The necessity, in some cases, to deliver milligram masses to the lungs rather than microgram masses has led to inhalation treatment times of up to 2-3 hours per day. This is to the detriment of patient comfort and, possibly, compliance. For instance, the Respimat™ metered-dose inhaler, is a small device in which two pressurized liquid jets collide to produce a fine aerosol with 11-15 µl being dispensed at each actuation (breath). However, it will only nebulize liquids, not suspensions. The dose per breath is very limited and the aerosol will readily change in size due to evaporation. There are numerous jet-type nebulizers available with perhaps the ePARI, PARI LC Star™ and the Aerotech II™ representing the best of these. These nebulizers have fluid flow rates of up to 0.89, 0.62 ml/min and 0.39 ml/min, respectively, with the PARI LC and Aerotech II™ respectively, having 80% and 77%, particles being less than 5 µm in diameter. Typically, jet type nebulizers produce aerosols with geometric standard deviations of about 1.8-2.3. The polydispersity does not make them ideal for the delivery of drugs to the lower respiratory tract; however they are relatively inexpensive. The markedly higher dose rate (4-5 ml/min) provided by the use of an aerosol processing and inhalation system, APIS will result in reduced treatment times.

Reduction in Shear Degradation

Some polymeric molecules and biologics are sensitive to shear degradation and consequent loss of desired activity. Shear degradation can be minimized by the generation of droplets which are too large to penetrate into the respiratory tract.

Delivery of Sparsely Soluble Agents

Some agents are sparsely soluble. In these cases, both large volumes of fluid and long inhalation times are required to deliver an effective dose of the active agent. The controlling (critical) parameters are a) the liquid flow rate b) the total input of unsaturated air and c) the output particle size. The initial size of the aqueous/solvent-based aerosol generated is dependent on the mass of the agent in solution or suspension such that on complete evaporation of the solvent, the residual particles have aerodynamic diameters between 1 and 7 µm. For example, a sparsely soluble compound will require the generation of very large droplets whereas very soluble compounds such as NaCl or sugar require the generation of smaller droplets. To optimize the rate of drug delivery the aqueous solvent flow rate should be 1-5 ml/min. Thus, aerosol generators should be chosen to generate the optimal size droplets such that on evaporation a solid phase aerosol of the desired respirable size, typically between 1 and 7 µm aerodynamic diameter results.

Alternate Method for the Generation and Delivery of Dry Powder Aerosols

Suspension of powders to form respiratory aerosols is difficult and sometimes impractical due to the surface forces between the molecules and agglomeration of the composite particles. Excipients are used to help facilitate aerosolization but these reduce the drug load per particle. Dry powder inhalers can require relatively rapid inhalation rates of 1 l/sec to disperse the powder, resulting in bronchial rather than deep lung aerosol deposition. Due to formulation issues, the drug and the inhaler are often designed to work together. There are several hand held devices available, including Rotahaler™ Turbuhaler™ and Diskhaler™. The Nektar™ dry power inhaler uses an independent power source to disperse the powder from a "blister". The powder contains drug particles (<5 µm MMAD), lactose or glucose particles (>30 µm diameter) or micronized particles. Typical doses delivered range from 4 to 450 µg with the Nektar product, providing 2-5 mg of solids per puff.

Compact Design

Large devices have obvious disadvantages in use. For example, an evaporator/concentrator previously described, (Pillai, R. S., Yeates, D. B., Eljamal, M., Miller, I. F. and Hickey, A. J. Generation of Concentrated Aerosols for Inhalation Studies. J. Aerosol Sci., 25(1):187-197, 1994.) had a volume of 200 l and was 5 ft long and 1 ft in diameter.

Inhalation Regulated Aerosol Delivery-Respiratory Aerosol Control System, RACS

Manually operated and breath-activated metered dose inhalers are the most commonly used devices for aerosol administration of medications. In a manual metered dose inhaler the drug delivery is manually activated by the patient. This requires the patient to have good coordination skill to operate these devices for efficient drug delivery. It is estimated that more than half of patients are unable to use the device properly and efficiently. Major problems with a manual metered dose inhaler include timing coordination between activation of drug delivery and inspiration of aerosol medication, multiple activation of drug delivery during inspiration, improper breath-holding, and operation difficulty with insufficient hand strength (young child, elderly or seriously ill). Another problem with metered dose inhalers and dry powder inhalers is that the inspiratory effort required to activate drug release results in a high inspiratory flow that causes excess aerosol deposition in the oral cavity and larynx. All these limitations make these manual metered dose inhalers sub-optimal for delivering aerosol medication.

Delivery of aerosolized agents has generally been limited to a given mass of fluid that is aerosolized at the beginning of each breath. When the mass aerosolized is independent of the size and depth of breathing, optimal use of the patient's breathing pattern is not utilized to achieve maximal delivery of the drug. Some devices are either operator-activated or activated by the flow caused by the initiation of the breath. In these devices a set dose is delivered independent of the size of the breath. In many situations the drug solution is placed in the reservoir of a nebulizer and the patient is instructed to inhale the medication until the medication has been completely aerosolized. The mass of drug leaving the nebulizer and that deposited within the desired region of the respiratory tract can vary greatly depending on the technique. These methods do not provide a dose which is dependent on breath volume. The inhaled volume is, in part, determined by the size of the patient.

To provide a better inhaler for aerosol delivery of medication, a variety of delivery systems and methods have been attempted and are the subject of U.S. patents. The major focus of these patents has been the provision of a breath-activated apparatus for the timing of the actuation of a metered dose inhaler, MDI and the assessment of inspiratory flow using a) measurements of the pressure drop across a resistive element b) a Venturi flow meter or c) the negative pressure caused by an inspiration. This signal has been used to regulate the valve on an MDI and provide flow and volume information to the user. These patents include:

Nichols, et al (U.S. Pat. No. 6,491,233; U.S. Pat. No. 6,854,461) discloses an aerosol generator and breath-activated methods of delivering an aerosol, in which the aerosol is generated by heating a medicated fluid as it flows through a capillary tube. It utilizes a pressure drop to trigger delivery of a given dose of the aerosolized agent at the beginning of a breath. Once the pressure drop is detected, the aerosol can be delivered to the user. However, this system and method makes no provision for concentrating the generated aerosol particles, as does the present invention. It also makes no provision for an outlet for the patient's exhalation and a constant air supply, so that the patient must disconnect his/her mouth from the mouthpiece for the next inhalation. It is unsuitable for operation as a respiratory control delivery device in conjunction with APIS which has a constant air supply flowing through the concentrator and a positive pressure at the output.

Cox, et al (U.S. Pat. No. 6,516,796; U.S. Pat. No. 6,557,552) discloses an aerosol generator and methods for using it. The generator comprises a heated flow passage, a source of material to be volatilized, a valve to regulate material flow, and a pressurization arrangement to cause material to flow. However, this method makes no provision for concentrating the generated aerosol, as does the present invention.

Poole (U.S. Pat. No. 6,158,431) discloses a portable system and method for delivering therapeutic material to the pulmonary system, comprising a droplet dispersion chamber, a droplet generating assembly, an assembly for heating and evaporating the droplets, and a delivery system. However, this system and method makes no provision for producing monodisperse aerosol particles in the optimum 1-7 µm diameter size range, nor does it make any provision for concentrating the generated aerosol particles, as does the present invention.

Lloyd et al. (U.S. Pat. No. 5,469,750) and Goodman et al. (U.S. Pat. No. 5,813,397) disclose a breath-activated microcontroller-based apparatus for delivery of aerosol medication for inspiration from a metered dose. However, this apparatus makes no provision for providing an outlet for the patients' exhalation and a constant air supply flowing (such that patients have to disconnect their mouth from the mouth piece for the next inhalation). The present invention enables continuous breathing without the necessity to disconnect from the device.

In all of the above-reported systems, the primary focus has been the development of hand-held devices which deliver doses of up to a few micrograms of active drug per breath. None of the systems and methods described in U.S. patents or in the literature for commercially available products deliver aqueous-based respirable aerosols at high dose rates of over a milligram of active agent per breath as a qeometically stable solid phase aerosol. The technology and methods that are the subject of this invention are particularly suitable for delivery of aqueous-based aerosols containing large molecules, genetic material and other therapeutic agents to the pulmonary system.

Thus, there is a need for a new aerosol processing and inhalation system that is suitable for delivery of aqueous-based aerosols containing large molecules, genetic materials and other therapeutic agents to the pulmonary system at a high dose rate, and in a manner that is both therapeutically effective and comfortable for the patient. The present invention provides a method and system for generating 10-30 µm aqueous or nonaqueous droplets, evaporating solvent from the droplets, and concentrating the aerosols to produce 1-7 µm aerodynamic diameter dry particles. By removing most of the carrier air and the unwanted vapor, respirable aerosols are delivered at a high dose rate.

SUMMARY OF THE INVENTION

APIS is designed to deliver aqueous- or nonaqueous-based aerosols at a high dose rate. In a preferred configuration, a large aqueous aerosol with droplets 10-30 µm in diameter is generated using one or more jet-type aerosol generators, enabling the generation of large molecules and biologics while minimizing the risk of shear-induced degradation. Other aerosol generators can be used. The aerosol jet is arrested by virtual impaction with a warm coaxial counter flow air jet in the opposite direction, and is rapidly evaporated with a warm swirling annular air flow within the evaporation chamber. Aerosol deposition on the chamber is minimized by the use of sheath air. The evaporation of an aqueous solvent can be further enhanced by convective heat transfer, and when necessary, the use of radiative heat transfer such as an infrared source with or without infrared reflectors to enhance the effect. The resulting residual dry particles with mass median aerodynamic diameter (MMAD) of about 3 µm are concentrated using a passive virtual impactor, PVI. Most of the dilution air and the unwanted vapor are removed through the exhaust ports of the PVI. The resulting small fraction of the air passing through the virtual impaction plates carries most of the dry particles and flows toward the output.

APIS results in geometrically stable dry particles containing up to 100% active agents.

Aerosol production can be regulated during inhalation using a respiratory aerosol control system and providing flow derived visible indicators.

BRIEF DESCRIPTION OF THE DRAWINGS

For a better understanding of the present invention, reference is made to the accompanying drawings, which are incorporated herein by reference.

DETAILED DESCRIPTION

Figure 1:
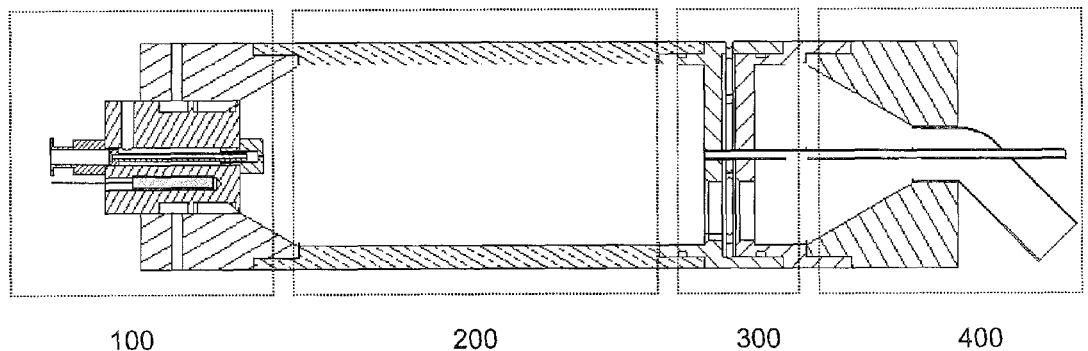
FIG. 1 is the assembly drawing of the invention in one of its preferred configurations.

The present invention relates to a method and system for aerosol processing and the inhalation control for generation and evaporation of agents dissolved or suspended in a fluid with a vapor pressure similar to or greater than that of water, and their subsequent concentration and controlled delivery as solid phase respirable aerosols. To perform these tasks, the invention generates relatively large droplets (10-30 µm) with a relatively narrow size distribution at fluid flow rates up to 5 ml per minute. The liquid is evaporated from the droplets, and the resulting aerosol, containing ~3 µm mass median aerodynamic diameter particles, is concentrated by a passive virtual impactor aerosol concentrator to provide a concentrated respirable aerosol. The mechanism to control the delivery of aerosol to a patient throughout each inspiratory cycle at a self-regulated flow rate is contained within the method and system. The method and system is able to provide at least 1 mg/breath of therapeutic aerosol with a particle mass median aerodynamic diameter (MMAD) of approximately 3 µm. This system, when used as recommended by the practitioner, maximizes the mass of aerosol deposition and provides improved reproducibility of the generated aerosol deposited within the subject's respiratory tract within a much shorter period of drug administration than is possible with other technologies.

The Aerosol Processing and Inhalation System, APIS and its clinical counterpart SUPRAER™ described herein is suitable for the evaporation of aqueous and/or nonaqueous solvents of high vapor pressure, such as water or alcohol from solutions or suspensions, and the concentration of the resulting 1-7 µm aerodynamic diameter residual solid particles and their delivery to the respiratory tract at inspiratory flow rates of 10-90 l/min, preferably 15-30 l/min. Aqueous liquid flow rates are typically between 1 and 5 ml/min with input air flow rates totaling 200 to 300 l/min. It is recognized that aerosol generation and processing systems are often specific to an active agent/solvent combination and to the properties of these, both individually and in concert. While the APIS does not provide a panacea for all aerosol delivery applications, it does enable many unresolved issues related to the delivery of aerosolized drugs and biologics to be overcome. These issues and their resolution by the invention described herein are addressed below.

The APIS reduces the size of these large droplets while minimizing shear degradation to provide solid aerosols within the respiratory range. Aerosol generation of small particles requires more energy and higher shear forces than is required for the generation of larger particles. The use of the APIS in conjunction with a large aerosol generator, such as those demonstrated in the examples herein, enables the generation of large molecules and biologics while minimizing the risk of their shear-induced degradation. It provides, following the evaporation of the fluid carrier, a respirable aerosol comprised of the residual solids. This configuration enables a high respirable drug load of solid phase aerosol particles with a good deposition probability to be generated for sparsely soluble compounds. Respirable particles of 1-7 µm aerodynamic diameter can be targeted.

The use of the APIS enables these agents to be generated as solutions potentially without the use of excipients and enables delivery of 100% of the active agent as a solid phase aerosol in an effort-independent manner at low inhalation velocities.

The APIS is 12 inches long and 3.5 inches in outer diameter with the aging chamber having an internal diameter of 3 inches and length of 6 inches. To achieve this marked reduction in size, the APIS combines multiple features to "condition" and concentrate the aerosol within a relatively small device. To achieve this end, the APIS contains several novel features. The aerosol generation jet is arrested, dispersed and partially evaporated with a coaxial counterflow air jet. Evaporation of the solvent is augmented by a sheaf of swirling airflow. The counterflow air jet and the sheaf of swirling air are warmed to further augment evaporation. Combined, these augment the evaporation of the aerosol through increased mixing which increases the energy transfer to the droplet to provide the latent heat of evaporation. This design also results in a more uniform transit time of the particles through the aging chamber.

The APIS is the only "hand held" or compact bench aerosol delivery device to include a passive aerosol concentrator. This concentrator is a small nine radial slit virtual impactor which requires no negative air suction to remove the unwanted air and solvent vapor. The output has a slight positive pressure which assists the patient's inhalation. This obviates the effort dependent dispersion of dry powders and their subsequent proximal deposition due to their rapid inhalation. When using aqueous based aerosols, concentration factors of 6 are typical.

The use of the APIS in conjunction with a respiratory aerosol control system, RACS, enables the delivery of the medication throughout the breath together with both the optimization of inhalation rate and measurement of the volume of active agent delivered. This results in both reduced treatment times and greater accuracy of the metered mass of the agent delivered to the respiratory tract. This is predicted to provide improved patient outcomes with less overdosing-related toxic and side effects.

An object of the invention is to provide a method for delivering aqueous-based aerosols at high dose rates, higher than present commercial nebulizers by a factor of 4-10.

Another object is to provide a method for delivering, surfactant, substantial masses of sparsely soluble agents, large molecules such as DNA, plasmids, liposomes and viral vectors.

An object of the invention is to provide a breath-activated respiratory aerosol control system for aerosol flow regulation when the clinical version of the invention (SUPRAER™) is used to deliver medication to patients.

Another object of the invention is to provide a simple, visible and cheap readout to directly measure and monitor the amount of medication remaining in the drug container during medication delivery.

It is another object to provide two different types of readouts for the aerosol control system: a LED bar dosage readout and a translucent window readout for direct visualization of the cartridge reservoir.

Another object of the invention is to measure respiratory flow using a differential pressure transducer and to simultaneously detect if the patient's mouth is connected to the mouthpiece or if the pressure signal is not measured with a pressure transducer within the flow tube. The outputs of these devices are utilized for monitoring breathing patterns and respiratory flow, and for operation of a pinch valve to automatically release active agent during inspiration.

Another object of the invention is to monitor the inhalation flow with a series of yellow, green, and red LEDs, which indicate that an inhaled flow is not yet high enough, in the range of an optimum flow, or too high, respectively. This provides a visual signal for the patient to control his/her breath pattern for optimal effect of aerosol delivery of medication.

Another object of the invention is to automatically deliver medication into the aerosol generator for aerosolization when a patient's inhalation flow detected by a differential pressure transducer is greater than a preset threshold and the patient's mouth is connected to the mouthpiece, which is detected by a pressure transducer. In the event that the patient's respiratory flow is insufficient to activate drug delivery, the preset threshold can be decreased by a threshold adjustment knob.

Another object of the invention is to apply two signals, flow rate and mouth-on, simultaneously measured by a differential pressure transducer and a pressure transducer, for decision making with regard to fluid delivery. The pressure at the output of the passive aerosol concentrator is positive, i.e. above atmospheric pressure, in both mouth-on and mouth-off states, so the mouth-on detection is required to avoid incorrectly delivering medication in the mouth-off state.

Another object of the invention is to apply a normally closed solenoid pinch valve for control of breath-activated drug delivery, in which fluid contacts only a piece of tubing that is squeezed by a solenoid. This provides a conveniently operated drug delivery controller for high-purity fluid applications.

Another object of the invention is to provide a breath-activated inhaler for patients to breathe normally during aerosol inhalation therapy. It is another object to deliver variable amounts of the entire dose of medication proportional to the amount of the patient's inspiratory time in one breath cycle. The longer the inspiratory period, the more medication delivered in one breath cycle.

Another object of the invention is to provide a breath-activated battery-powered electronic apparatus for the respiratory aerosol control system, which is designed with low-power and low-cost electronic elements housed in the SUPRAER's case. This reduces the cost of production, thereby making the device available to a greater number of users.

A feature of the invention is that the size of the initial droplets generated by the atomizer/atomizers can be chosen to obtain dry particles with a mass median aerodynamic diameter of about 3 µm.

Another feature of the invention is that the pressure, flow, temperature and dimensions of the heated coaxial counter flow air jet, and the heated swirling annular dilution air jet can be adjusted with consideration of the desired solution, particle size and dose rate.

Another feature of the invention is that the dimensions of the passive virtual impactor aerosol concentrator can be chosen with consideration to the flow rate and particle size desired to obtain the maximum aerosol delivery efficiency.

An advantage of the invention is that patient treatment times can be shortened due to higher dose rate drug delivery.

An advantage of the invention is that it can deliver respirable geometrically stable particles for respiratory drug delivery (aerodynamic diameter ~1-7 µm), consistent with a maximum drug load.

An advantage of the invention is that the inhaled particles can contain up to 100% of the active agent.

An advantage of the invention is that the production of initially large particles requires less energy than small particles, resulting in lower shear stresses.

An advantage of the invention is that aerosol generators which produce large particles can be incorporated, minimizing the degradation of large molecules such as DNA, plasmids, liposomes and viral vectors can be avoided. This can be achieved with microfluidic focused flow.

An advantage of the invention is that the particle size and fluid flow output are easily adjusted.

An advantage of the invention is that the passive virtual impactor aerosol concentrator can remove most of the air and unwanted vapor, thus preventing the vapor from condensing and thereby maintaining a geometrically stable particle size. This is particularly well achieved using the two stage concentrator described herein.

An advantage of the invention is that a small positive pressure of the PVI can reduce the effort by the patient.

Another advantage of the invention is that the solvent can be typically water, alcohol or other volatile solvent such as hydrofluoroalkane for hydrophilic and lipophilic drugs.

Another advantage of the invention is that the heated coaxial counter flow air jet which arrests the high velocity aerosol jet augments the mixing of aerosol and thus its evaporation. This markedly reduces the length of the device.

Another advantage of the invention is that the heated swirling annular dilution air jet surrounding the aerosol jet augments the mixing of aerosol and thus its evaporation.

Another advantage of the invention is that the heated swirling annular dilution air flow surrounding the aerosol jet reduces impaction of aerosol onto the inner wall of the chamber thereby increasing aerosol delivery efficiency.

Another advantage of the invention is that the respiratory aerosol control system can automatically deliver drugs to the aerosol generator during inhalation and enable the patient to monitor inhalation flow rate so as to achieve the maximum aerosol delivery efficiency.

Another advantage of the invention is that the aerosol generator can be comprised of many jet-type aerosol generators which generate large particles.

An aspect of the invention is that the solution containing the active agent is contained in a cylindrical corrugated collapsible bag. This provides a uniform pressure and thus constant fluid flow is ensured by the fixed diameter of the corrugated bag, yielding a constant area for compression. A low compliance delivery tube enables the drug flow to a microfluidic focused flow aerosol generator to be controlled by a pinch valve. This can be sterilized and disposable resulting in greater patient safety and compliance.

Another advantage of the invention is that it enables the aerosol to be delivered to the patient only during optimal inhalation flow and for the entire duration of this optimal inhalation flow while monitoring the dose delivered. This reduces treatment time and increases the consistency of the dose delivered to the respiratory tract. Also, the ability of the patient to optimize inspiratory flow increases the deposition efficiency within the targeted region of the respiratory tract.

The detailed descriptions provided herein are for illustrative purposes only, and should not be construed as limiting the scope of the invention as described in the appended claims.

The assembly drawing of the invention is shown in FIG. 1. It comprises: 1) an aerosol generation system 100, 2) an aerosol evaporation system 200, 3) an aerosol concentration system 300 and 4) an aerosol output system 400. In another of its preferred configurations a Respiratory Aerosol Control System RACS shown in FIG. 7 a structure 405 replaces structure 400.

Aerosol Generator

Figure 2:
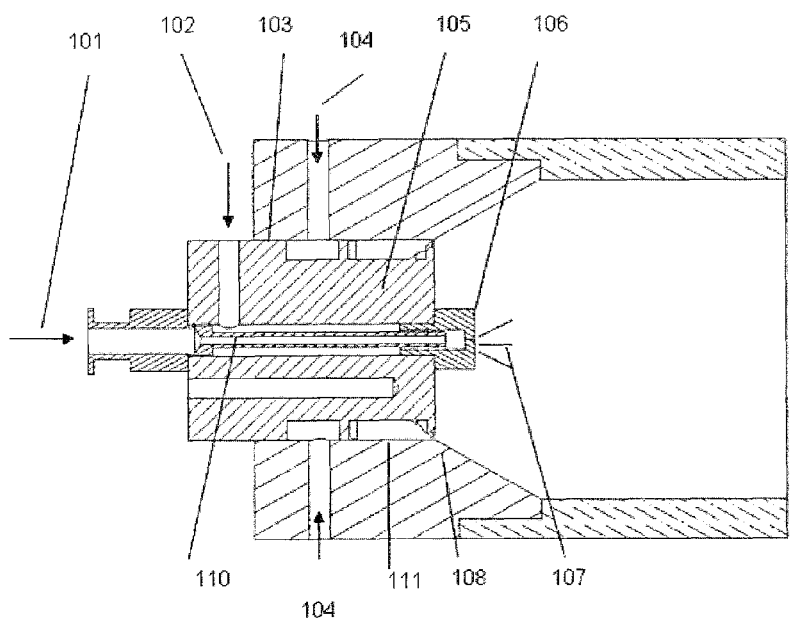
FIG. 2A is a schematic drawing of a single-orifice microjet aerosol generator.
FIG. 2B is a CAD design of a single orifice aerosol generator.
Figure 2:
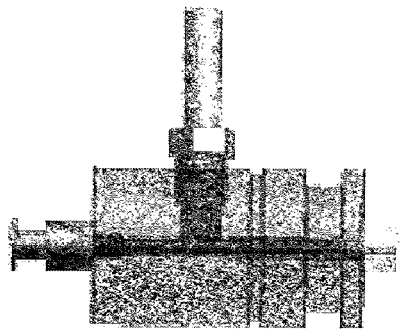

The initial diameter of the aqueous/solvent-based aerosol generated is governed by the mass of the agent, in solution or suspension, that on complete evaporation of the solvent, will result in residual particles with aerodynamic diameters between 1 and 7 μm. For instance, a sparsely soluble compound requires the generation of large droplets whereas very soluble compounds such as NaCl or sugar require the generation of smaller droplets. The initial size will also be dependent on the density of the residual particles. To optimize the rate of drug delivery, the aqueous solvent flow rate should be about 1-5 ml/min. Thus, many aerosol generators can be used in conjunction with APIS. A Microjet aerosol generator 100 in FIG. 1 and detailed in FIG. 2A, is for purposes of illustration and should not be construed as limiting the scope of the present invention. In this case, aerosol is generated with a single orifice fluid input system in which the resulting jet of aerosol is arrested and diluted by a coaxial counter flow jet. The dilution of the jet is augmented by the addition of a sheath of swirling air. Higher flow rates or smaller particles can be achieved using an aerosol generator with multiple orifices.

A single-orifice aerosol generator shown in FIG. 2A consists of: a capillary tube (stainless steel tubing) 105; an orifice plate (stainless steel) 106; an aluminum body 103; a compressed air source 102; a dilution air source 104, a cartridge heater 110; air flow channels 111, a Teflon cone 108 and a fluid supply system 101. A CAD design for the single aerosol generator is shown in FIG. 2B.

Aerosol generation of small particles requires more energy and higher shear forces than that of larger particles. Thus APIS, when used in conjunction with a large particle aerosol generator, enables the generation of large molecules and biologics while minimizing the risk of their shear-induced degradation, and provides a resultant respirable aerosol. This configuration also enables sparsely soluble compounds to be generated with a high respirable drug load of solid aerosol particles with a good deposition probability. Final respirable particles size of 1-7 μm aerodynamic diameter can be targeted.

Figure 3A:
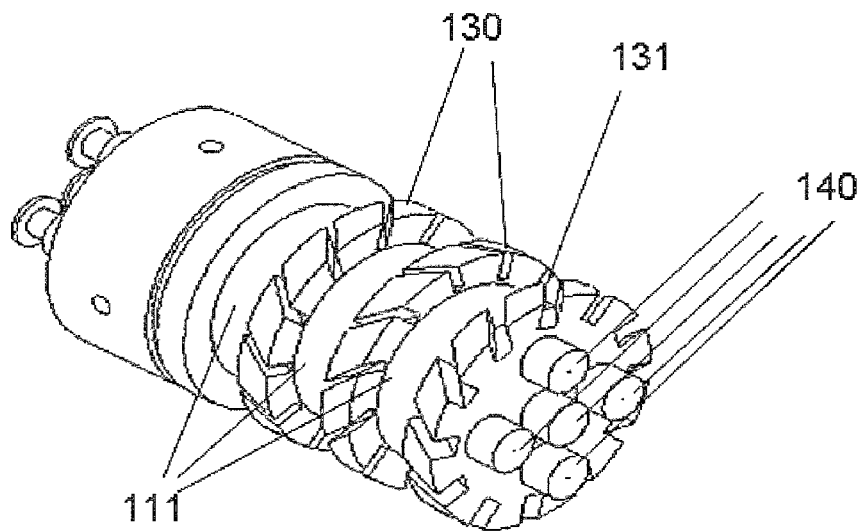
FIG. 3A is a schematic drawing of a multi-orifice microjet.
Figure 3B:
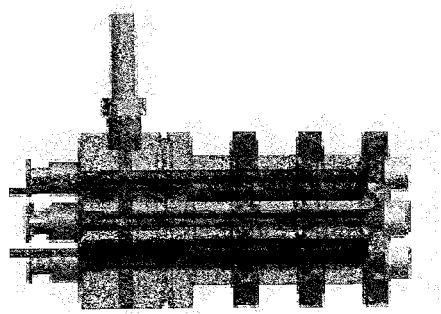
FIG. 3B is a CAD design of a multi-orifice aerosol generator.

A multi-orifice aerosol generation system is illustrated in FIG. 3A. For illustration purposes only, the following refers to a 5-orifice system. FIG. 3B is a CAD design for a 5-orifice aerosol generation system. There are opposing directional vanes 130. These are designed to maximize the heat transfer from the heater to air flowing through the generator 111 FIG. 2A and FIG. 3A. The last stage of vanes 131 causes the swirling sheaf of air designed to augment the mixing and drying of the liquid aerosol.

Aerosol Evaporator

Figure 4:
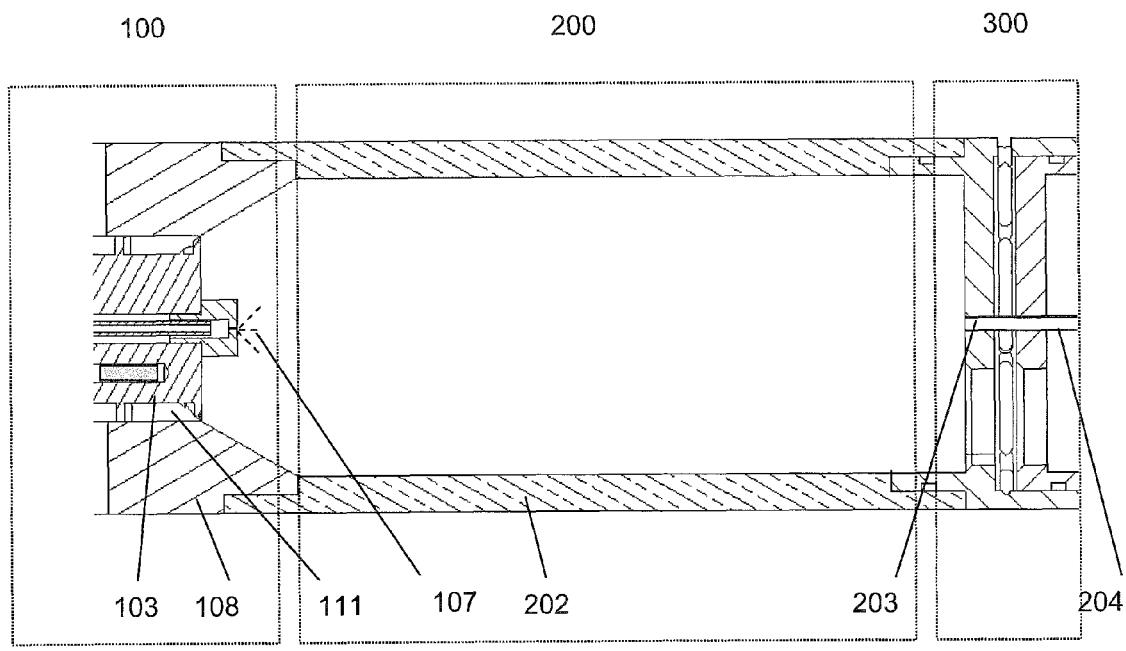
FIG. 4 is a schematic drawing of the aerosol evaporation system.

The aerosol processing and inhalation system contains several features to augment the evaporation of these 10-30 μm droplets in a small volume evaporation chamber FIG. 1 200 as also shown in more detail in FIG. 4 an aerosol generation jet 107 is arrested, dispersed and partially evaporated with a coaxial counterflow jet 203 emanating from a counterflow tube 204 at the opposite end of an evaporation chamber 202. Evaporation of the solvent is augmented by a sheaf of swirling airflow entering the evaporation chamber 202 between the aerosol generator body 103 and a Teflon input cone 108. The counterflow jet 203 and the sheaf of swirling air can be heated to further augment evaporation. Combined, these augment the evaporation of the aerosol through increased mixing and increased energy transfer to the droplet to provide the latent heat of evaporation, as well as a more uniform mean transit time of the particles through the aging chamber. The aging chamber 202 has an internal diameter of 3 inches and length of 6 inches. An aerosol generator 103 fits snugly into the Teflon input cone 108. The coaxial tube 204 protrudes through the center of the aerosol concentrator 300. This enables the counter-flow air jet 203 to arrest the aerosol generation jet(s) 107 so that a) the particles in the aerosol jet do not impact on the "walls" of the concentrator, and b) the mean residence time of the droplets in the chamber is increased. The input air pressure, flow rate, temperature and dimensions of the counter flow air jet can be adjusted to optimize the stagnation surface location with consideration of, a) the nozzle air flow rate, b) the liquid flow rate and c) the total input of unsaturated air.

The inclination of the heat transfer vanes 130, as shown in FIG. 3A, on the aerosol generator body with respect to the central axis is 60°. Each channel is 0.2 inch deep, 0.0625 inch wide and 0.5 inch long. The air velocity through the vanes is 52 m/sec when the air flow is 300 l/min. The swirling flow establishes high mixing rates between the cone shaped aerosol jet and a heated swirling annular air stream. Heat transfer, mass transfer and evaporation all increase due to enhanced convective mixing. The dimensions of the chamber can be reduced from 6 inches long by 3 inches internal diameter through the addition of a radiant infrared lamp (not shown) adjacent to the evaporation chamber 202. This can be further optimized by the use of an infrared reflector. The dimensions of the aging chamber can be adjusted based on a) the liquid flow rate b) the total input unsaturated air and c) the initial droplet particle size. One liter of air at 20° C. holds 18 mg of water whereas one liter of air at 33° C. holds 36 mg water. Thus, by heating the inspired aerosol from 20° C. to 33° C., up to twice the mass of water can be evaporated from the aqueous aerosol. Water has a strong absorption band in the near infrared (IR) at 975 nm. Thus infrared radiation emitted from a lamp at this wavelength will be preferentially absorbed by the aqueous particles until the water has been evaporated from the particles. Forty Watts are required to evaporate 1 ml/min of fluid flow.

Aerosol Concentrator

Figure 5:
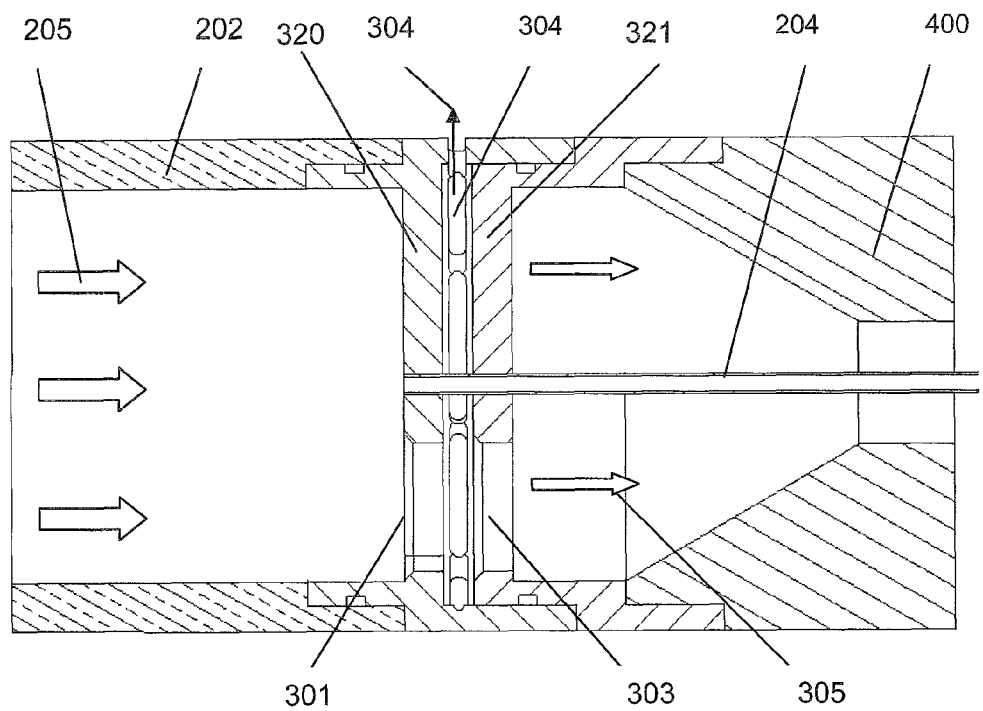
FIG. 5 is a schematic drawing of a single-stage aerosol concentration system.

APIS is the only "hand held" or compact bench aerosol inhalation delivery device to include a passive aerosol concentrator. The aerosol concentrator system assembly is shown in FIG. 5. It is comprised of two plates, a face plate 320 and a virtual impaction plate 321. This concentrator has nine radial slit nozzles 301. This virtual impactor which requires no negative air suction to remove the unwanted solvent vapor from between the nozzles 301 and the virtual impactor plate 321. The output has a slight positive pressure which assists the patient's inhalation ability. This obviates the effort-dependent dispersion of dry powers and their subsequent proximal deposition due to their rapid inhalation. The mechanism of aerosol concentration by virtual impaction utilizes the high inertial momentum of aerosol particles as compared to air. An aerosol 205 from the chamber is directed into the large end of slit nozzles 301. Opposite the outlet at the small end of the nozzles, separated by a small gap 304, is a virtual impaction plate 321 positioned with open slits 303 aligned with the nozzles 301. The major fraction of the air and vapor 304 exits from a gap 304 between the nozzles and virtual impaction plate. The remaining small fraction of air 305 containing the 1-7 μm aerodynamic diameter particles passes through the slits 301 in the virtual impaction plate. These residual solid particles have a geometrically stable diameter and thus predictable deposition characteristics in the respiratory tract.

Based on a cutoff aerodynamic diameter of 3 μm (density=1000 kg/m$^3$) and particles with input air flow rates of 200 and 300 l/min, respectively, the calculated dimensions of the nozzles are shown in Table 1. The width of the rectangular impactor, W, is considered as a reference dimension. The distance between the nozzle and the plate S is S=1.5W, the thickness of the nozzle T=W, and the width of the slits 303 in the plate 321 aligned with the nozzles is 1.3W. The design incorporates nine slit nozzles radially arranged to have the capacity for processing large input volumetric flow rates (200 and 300 l/min).

TABLE 1

Parameters of concentrators

| | Cutoff Diameter (3 μm) | |
| --- | --- | --- |
| | 300 l/min | 200 l/min |
| Number of slit nozzles | 9 | 9 |
| Air flow rate thru a slit nozzle (L/min) | 33.33 | 22.22 |
| Width of slit W (cm) | 0.18 | 0.17 |
| L/W | 10 | 8 |
| Length of slit L (cm) | 1.8 | 1.36 |
| Air velocity at throat orifice (m/s) | 17.0 | 16.0 |
| Reynolds number | 3400 | 3500 |

The dimensions of the passive virtual impactor concentrator can be adjusted with consideration of the flow rate and particle size desired to obtain the maximum aerosol delivery efficiency.

Two Stage Concentrator/Evaporator

Figure 6:
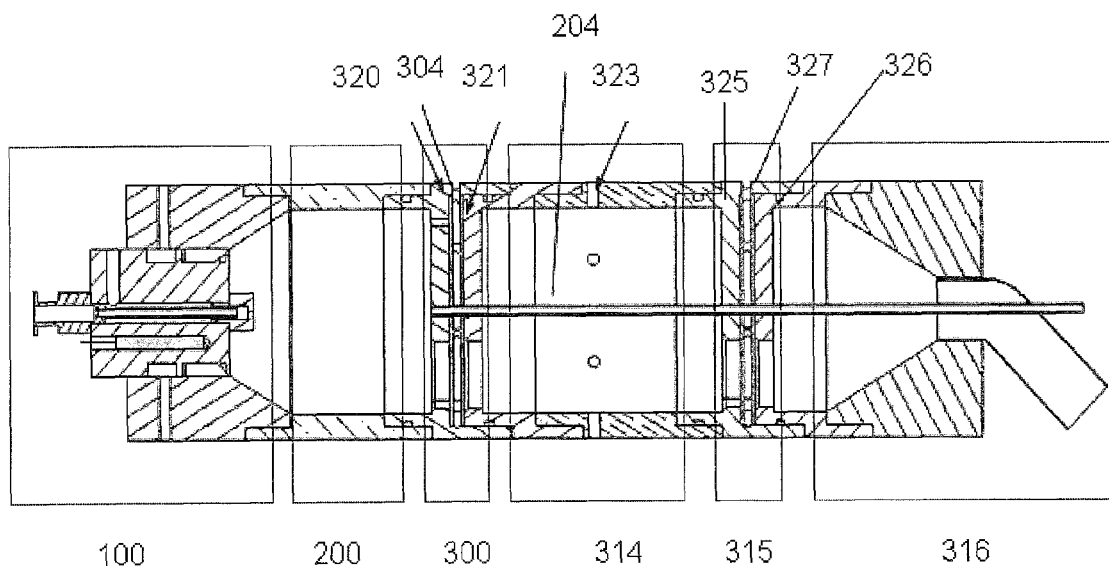
FIG. 6 is a schematic drawing of the device with a two-stage aerosol concentration system.

A two stage concentrator which includes the adding of additional air between the first and second stages is unique and a subject of this invention. In a one stage concentrator, it is a prerequisite that the exhaust air is at less than 100% humidity for complete evaporation of the aqueous aerosol to dryness. In the case of saline aerosol (aqueous sodium chloride solution) the humidity must be below 70% to ensure complete dryness of the residual salt particle. This requires very high dilution air flows. This airflow can be substantially reduced using a two stage device. The air removed during the first stage can be 100% humidified and thus, in the case of sodium chloride, either less total air is required or more saline solution can be aerosolized. For example, for a flow of 100 l/min into the first concentrator with a fluid flow rate of 5 ml/min and temperature of 34° C., 40 mg/l.times.100 l/min or 4 ml will evaporate. Dilution of the 20 l/min output containing approximately 1 ml of water with 80 l/min of dry air results in a relative humidity at the exit of the second stage of 1000 mg/100 l/min or 10 mg/l, or 25% relative humidity at about 34° C., thus insuring complete evaporation of the water from the sodium chloride solute. As the total airflow is only 200 l/min, the dimensions of the concentrator can be markedly reduced in both diameter and length and a smaller air pump can be used. The assembly drawing of the invention with a two-stage aerosol concentrator is shown in FIG. 6. It consists of: 1) the aerosol generation system 1400, 2) the 1st stage aerosol evaporation system 200, including the counter-flow tube 204 3) the 1st stage aerosol concentration system 300, 4) a 2nd stage aerosol evaporation system 314, 5) a 2nd stage aerosol concentration system 315, and 6) the aerosol output system 400. If 50% of the total input unsaturated air (e.g. 200 l/min) is injected at the first stage 200, and another 50% injected at 323 in the second stage 314, and the number of slits is maintained at 9, then the length of the slits can be reduced from 1.8 cm to 0.74 cm. The internal diameter of the concentrator/evaporation chamber can be reduced from 3 inches to 2 inches. The length of the evaporation chamber can also be shortened by using the two-stage aerosol concentrator because: (1) the velocity (0.82 m/s) of 100 l/min air flow in the 2 inch diameter chamber is lower than that (1.1 m/s) of 300 l/min air flow in 3 inch chamber, i.e., the evaporation time of the droplets is much longer in the same length chamber; (2) most of the vapor is removed from a small gap 304 between the first stage nozzles 301 in impactor plate 320 FIG. 5 and an impactor plate 321 as in the virtual impactor described above. The other 50% of the unsaturated air is injected 323 at the second stage 314 and mixes with only a small fraction of air carrying most of the particles, resulting in a lower vapor pressure/humidity and a high evaporation rate in the second evaporation chamber. Most of the air, together with the unwanted vapor, similarly is removed from a small gap 327 between a second stage nozzle 325 and impact plate 326. The remaining small fraction of the air carries the dry particles to flow toward the output as described for the one stage concentrator above.

The two-stage concentrator has been designed for the present invention, based on a cutoff aerodynamic diameter of 3 μm water (density=1000 kg/m$^3$) and particles at input air flow rates of 100 l/min. The dimensions of the nozzles are shown in Table 2. The width of the rectangular impactor, W, is considered as a reference dimension. The distance between the nozzle and the plate S=1.5W, the thickness of the nozzle T=W, and the width of the slits in the plates aligned with the nozzles is 1.3W The design incorporates 9 slit nozzles radially arranged to have the capacity for processing input volumetric flow rates of 100 l/min. TABLE-US-00002 TABLE 2 Parameters of two-stage concentrators Cutoff Diameter (3 μm) 100 l/min Number of slit nozzles 9 Air flow rate thru a slit nozzle (L/min) 11.1 Width of slit W (cm) 0.18 L/W 4.1 Length of slit L (cm) 0.74 Air velocity at throat orifice (m/s) 13.8 Reynolds number 2760

TABLE 2

Parameters of two-stage concentrators

| | Cutoff Diameter (3 μm) 100 l/min |
| --- | --- |
| Number of slit nozzles | 9 |
| Air flow rate thru a slit nozzled (L/min) | 11.1 |
| Width of slit W (cm) | 0.18 |
| L/W | 4.1 |

TABLE 2-continued

Parameters of two-stage concentrators

| | Cutoff Diameter (3 μm) 100 l/min |
|---|---|
| Length of slit L (cm) | 0.74 |
| Air velocity at throat orifice (m/s) | 13.8 |
| Reynolds number | 2760 |

Invention Assembly for Clinical Applications

Figure 7:
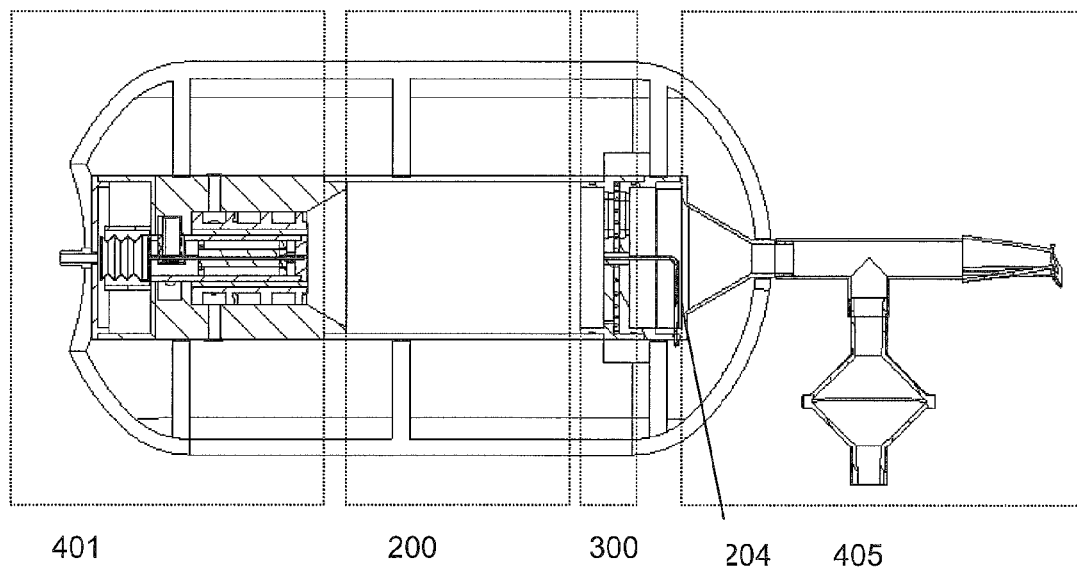
FIG. 7 is a schematic drawing of the aerosol processing and inhalable aerosol delivery system, for clinical applications.

The device that is the subject of this invention can be configured for clinical applications. This configuration, SUPRAER™, is capable of delivering inhalable aqueous-based aerosols containing large molecules or genetic materials at a high dose rate. A clinical or home use design of SUPRAER™ is shown in FIG. 7. The major components are 1) a drug reservoir cartridge and nebulization unit 401, 2) the evaporation chamber 200 including the counter flow tube 204, 3) the aerosol concentrator 300 and 4) a output flow delivery and regulation manifold 405 and Respiratory Aerosol Control System.

Figure 8:
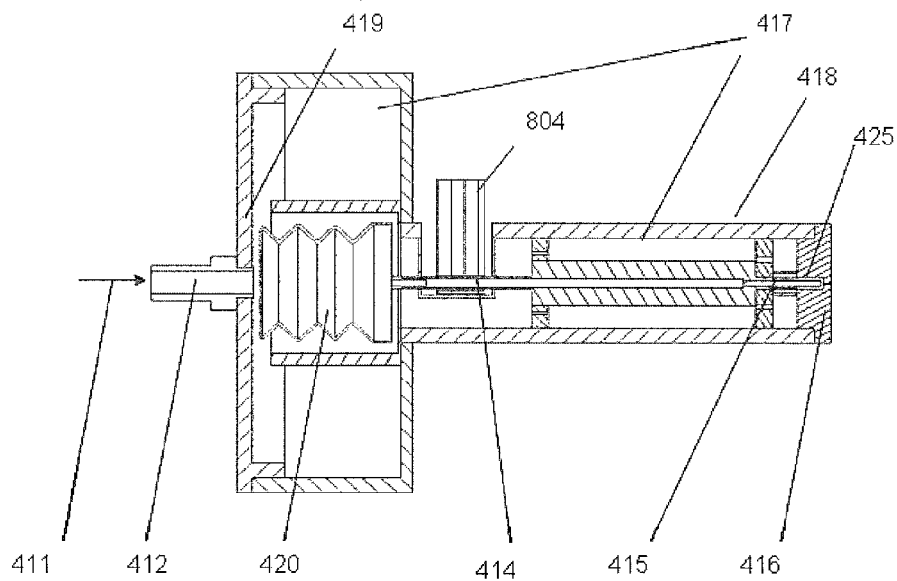
FIG. 8 is a schematic drawing of the disposable multi-use cartridge.

Most of SUPRAER™ is reusable and easy to clean. However, to avoid contamination and ensure proper drug dosage, a fluid reservoir, and focused flow fluidic aerosol generator has been designed into one single or multiuse disposable cartridge. A schematic of this cartridge is shown in FIG. 8. The drug is contained in a disposable collapsible bag 420, (an accordion-like collapsible bag) which is attached via a compliant capillary tube 414 to an aerosol generation head 425. A uniform pressure and thus fluid flow is ensured by providing a constant compressible surface area to the high pressure air. This forces the fluid through an orifice 416 at a constant rate. The orifice is opened prior to use using a "tear-off" seal. The pressure to drive the fluid through the orifice is also provided by the compressed air 411, thus eliminating the need for mechanical plungers and a stepper motor. A valve 804 is used to control the medication fluid flow to the aerosol generating orifice. This valve also prevents drug leakage when the nebulizer is not in use. The valve specifications should regulate an aqueous fluid flow of 0.1 to 10 ml/minute, at pressure differentials of 0-50 psi with actuation and deactivation times in milliseconds. It should also be usable with alcohols and be very small in size with minimal power requirements. A section of the capillary tubing 414 that is within the valve is very compliant with minimal elasticity. Thus the normally closed solenoid valve 804 with its side cut out can be used to positively control the fluid flow. A breath-activated respiratory aerosol control system for aerosol flow regulation activates and deactivates the normally closed two-way pinch valve 804 according to the breathing pattern (see FIG. 11). When the valve is activated the pressure in the reservoir forces the fluid through the capillary 414 to the orifice 41 for nebulization. On deactivation of the valve the fluid flow stops. The cut-out enables the tube to be placed in the path of the plunger without having to feed it through the valve. This results in a substantial increase in ease of use and functionality. The bag 420 can be easily replaced by removing the high pressure cover 41 and extracting the bag. When the new bag 420 is inserted the high pressure cover 41 is replaced. An identical total dose delivered can be readily achieved when all the drug solution including a given total dose rate (for one treatment) contained in the disposable collapsible bag is delivered to a patient. The cartridge FIG. 8 consists of 5 components: the bellows bag 420, the collapsible capillary tubing 41, the pinch valve 804, the orifice 41 and a support structure 418. The orifice 416 fits snugly with precision within the support structure 418 to ensure the coaxial nature of the fluid flow and the distance between the capillary tube 41 and the orifice 41. These are critical for proper and reproducible functioning of the aerosolizer.

The aerosol generators can be atomizers or nebulizers which generate aqueous aerosols of 10-30 μm with a narrow size distribution. They can be single orifice generators or multi-orifice generators. As noted, the air jet 203 from tube 204 (see FIG. 7) is installed opposite to the aerosol jets 107 FIG. 2A along the axis of the evaporation chamber 200 FIG. 1 and FIG. 4 to arrest the aerosol jets 107 FIG. 2A. When a non-jet type nebulizer is used, the counter flow air jet can be reduced in flow or eliminated. The interaction of the aerosol and air jets drives the flow stream direction towards the walls of the chamber. A co-axial co-flow annular air sheaf is also employed to minimize interception of the particles with the walls and increase the rate of droplet evaporation. The liquid containing the dissolved or suspended agent is driven to the capillary tube by pushing a collapsible bag 420 with compressed air 411, 417. The compressed air is supplied by a compressor (or high pressure $CO_2$ cartridge).

The aerosol evaporation and aging chamber 200, FIG. 1 and FIG. 7, is attached to the output of the aerosol generator 100 FIG. 1 to completely evaporate the droplets. To minimize the electrostatic deposition, the chamber is made of Pyrex glass, aluminum, or electrically conducting plastic. An infrared transparent "window" is installed along the chamber. An infrared lamp can be used to augment the rate of evaporation. To provide uniform flooding light to the aerosol, the light may be collimated using an Aspherab condensing lens system coupled with a broad band IR filter. All lenses are made of borosilicate crown glass which covers a transmission spectral range of 350 to 2500 nm. To maximize the energy transfer of the IR to the aqueous aerosol, the inside of the chamber can be provided with an infrared reflecting surface, e.g., 3M™ dichroic filter film, or painted with an infrared reflective paint.

Respiratory Aerosol Control System

Figure 9:
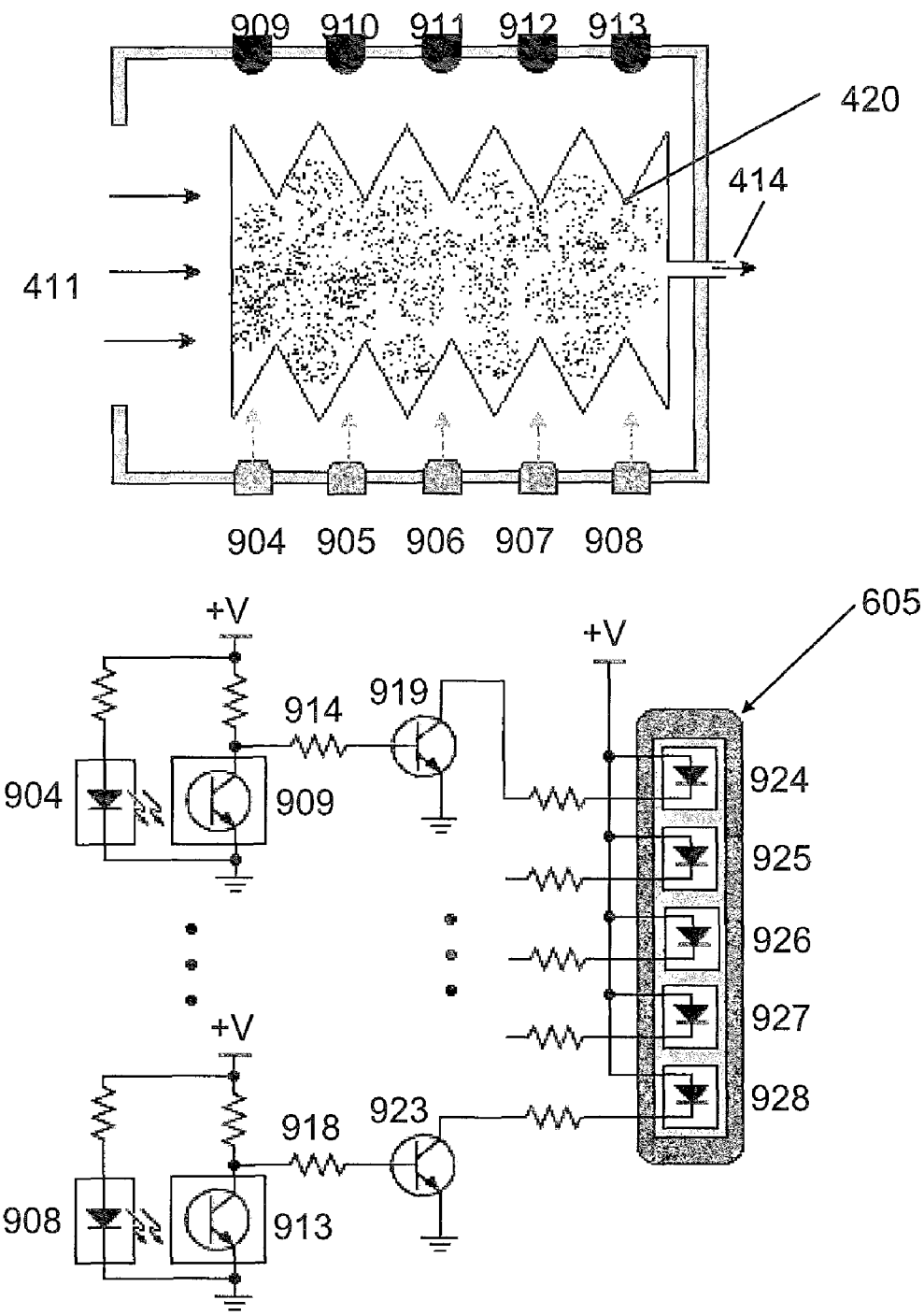
FIG. 9 is a schematic drawing of the dose monitoring system.

The respiratory control system for the regulation of both breathing pattern and fluid feed to the aerosolizing orifice is unique and a subject of this patent. A schematic diagram of a dosage monitoring system is shown in FIG. 9. A combination of LEDs and photoelectric cells, (see FIG. 9), installed in the compressed air chamber 417 FIG. 8 and FIG. 9 is used to detect the position of the collapsible bag and to provide a signal to a digital readout when the bag is empty. There are several LED's 904, 905, 906, 907, 908 and corresponding photoelectric cells 909, 910, 911, 912, 913. These are reusable. The volume of the drug solution in the bag 420 can be adjusted with consideration to the total dose desired. A LED bar readout 605 (see FIG. 9 and 924, 925, 926, 927, 928 FIG. 10B), is used to monitor the dose of medication remaining. The entire dose of drug fluid per treatment is contained in the disposable and squeezable bag 420, which is attached via the compliant capillary tube 414 FIG. 8 to the aerosol generator through the capillary tubing 214. When the pinch valve 804 (see FIG. 8) is opened, compressed air 411 forces the fluid in the bag 420 FIG. 8 through the capillary tube 414 at a constant rate into the aerosol generation head 425. The amount of dose delivered is detected by the 5 pairs of infrared emitters 904-908 and receivers 909-913 and shown on the LED bar dosage readout 605 comprised of 5 green LED diodes 924-928.

When the drug bag 420 is full of medication fluid, the infrared light from all 5 infrared light emitting diodes 904-908 is blocked by the bag 420, so no infrared light can reach the 5 infrared phototransistors 909-913. All 5 infrared phototransistors 909-913 are completely turned off. Thus, all 5 transistors 919-923, LED drivers of the LED bar dosage readout 605, get a base current via resistors 914-918, respectively. This puts all 5 transistors 914-918 in the saturation state with a maximum collector current. All 5 green LED diodes 924-928 of the LED bar dosage readout 605 driven by the transistors 919-923 are lit to indicate a full dosage of fluid.

When fluid is released in response to the patient's respiration, the fluid bag 420 is gradually compressed toward the right. When infrared light of an infrared light emitting diode, for example, infrared diode 904, is not blocked by the bag 420, the light will reach the relative infrared phototransistor 909. The phototransistor 909 reverts completely from the turn-off state to the saturation state with a collector-emitter voltage of near zero. This collector-emitter voltage of the phototransistor 909 is unable to provide enough base current to retain the transistor 919 in the saturation state. The transistor 919 inverts the saturation state to the turn-off state with a zero collector current. The LED 924 of the LED bar dosage readout 605 is off and all 4 other LEDs 925-928 stay on, which indicates a non-full dosage of fluid.

When the entire dose of fluid is delivered, the fluid bag 420 is collapsed. All 5 phototransistors 909-913 receive the infrared light from the 5 infrared diodes 904-908. Thus, all 5 phototransistors 909-913 are in the saturation state, which puts all 5 transistors 919-923 in the turn-off state. All LEDs 924-928 of the LED bar dosage readout 605 are thus off to indicate an empty dosage bag.

The aerosol exiting the chamber enters the large ends of nine radially arranged slit nozzles of the aerosol concentrator 301 as shown in FIG. 5. The virtual impaction plate 321 FIG. 5 with nine radially arranged slits is aligned with the slit nozzles. The small gap between the plates 304 enables 90% of the air to escape, leaving the remaining small fraction of air containing the aerosol to penetrate the virtual impaction plate, as previously described. Any particles in the exhaust air are captured by a filter and the particle-free air is exhausted into the ambient atmosphere. The design incorporates nine slits so as to have the capacity for processing input volumetric flow rates up to 300 l/min.

Figure 10A:
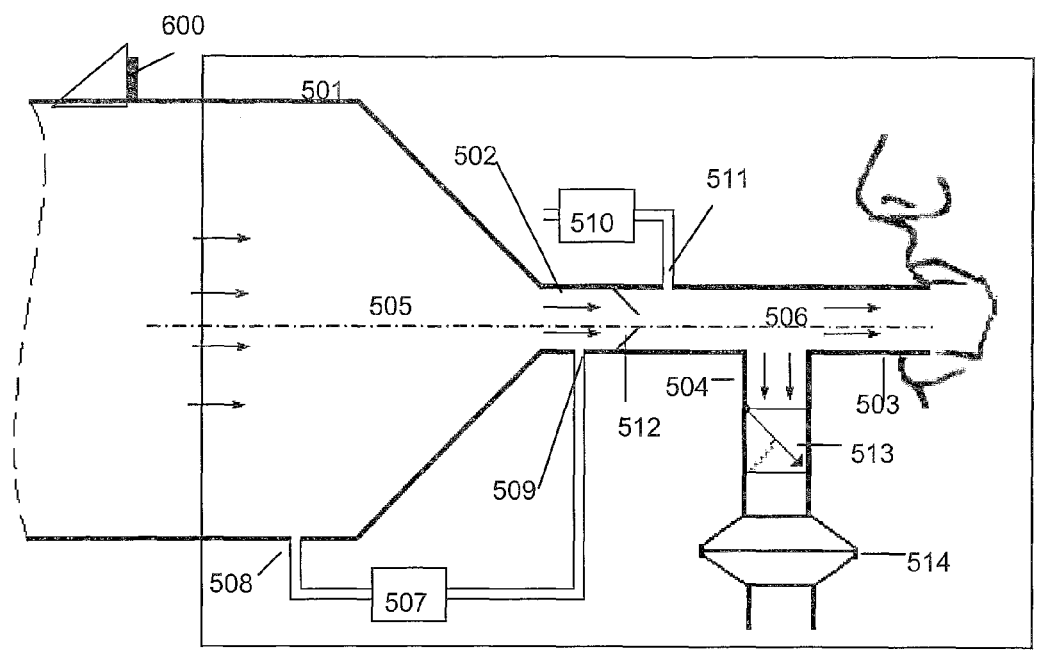
FIG. 10A is a diagram of the flow rate measuring system.

Finally, the flow is regulated by a Respiratory Aerosol Control System, RACS FIG. 10A. This system makes use of a differential pressure sensor 507 (Venturi effect flow meter), a one-way straight-through non-obstructive silicone valve 512 at the exit of the concentrator, a pressure sensor at the output 510 and a resistive exhalation valve 513. The aerosol inhalation flow, breathing pattern and aerosol generation are governed by logic circuits (see FIG. 12) which in turn activate both the flow indicator lights 605 FIG. 10B and inspiratory fluid flow and thus aerosol generation. These are further described below.

Figure 10B:
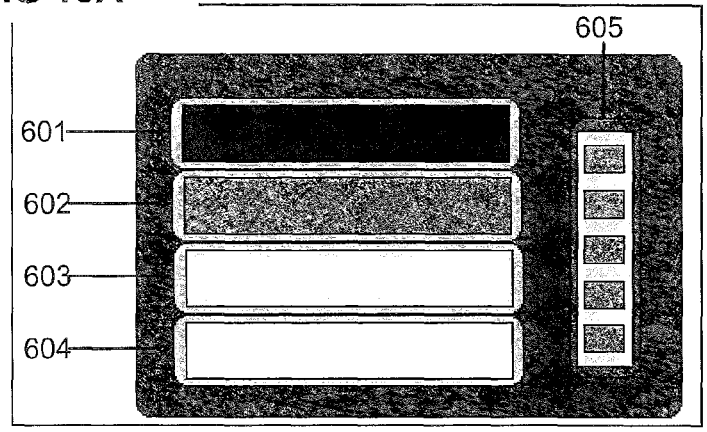
FIG. 10B is a diagram of a LED indicator for monitoring flow rate.

A diagram of an output air 505 flow rate measuring system is shown in FIG. 10A. The aerosol flow rate 505 is measured by a differential pressure 507 across a Venturi flow element 501-502 and monitored by a LED indicator This LED indicator is shown in FIG. 10B. The differential pressure transducer 507 has two pressure ports 508 and 509 in cylindrical tubes 501 and 502, respectively. The additional pressure sensor 510 has a pressure port 511 in a tube 502. A tube 504 with a valve 513 and a filter 514 provides an outlet for the patient's exhalation. The valve 513 is a normally closed one-way resistive check valve such that it does not open until a pressure threshold greater than a preset positive pressure is applied. The filter 514 is used to prevent any aerosol medication entering the ambient air.

Referring to FIG. 10A, the cylindrical cross section of the concentrated aerosol collection chamber 501 is larger than that of the tube 502 and a mouthpiece 503 connected to tube 502. When the flow goes from a flow path 505 of the concentrated aerosol collection chamber 501 to a flow path 506 of the tube 502 and the mouthpiece 503, the change of cross sectional areas causes an increase of flow velocity, resulting in a pressure drop. The pressure drop is measured by the pressure differential transducer 507 at ports 508 and 509 to obtain a measure of the flow rate. The transducer 507 provides a voltage proportional to the flow through path 506.

Referring to FIG. 10B, a LED indicator 600 FIG. 10A is shown in detail in FIG. 10B. It includes a series of yellow 603, green 602 and red 601 LEDs (XEM series, SunLED Corp.) which indicate that an inhaled flow is not yet high enough, in the range of an optimum flow, and too high, respectively. The range of the optimum flow is generally set from 250 to 400 ml/s.

The pressure in the tube 502 is measured by the pressure sensor 510 at port 511 and used to detect if the patient's mouth is connected to the mouthpiece 503. A white LED 604 is used to indicate that the patient's mouth is connected to the mouthpiece.

Figure 11:
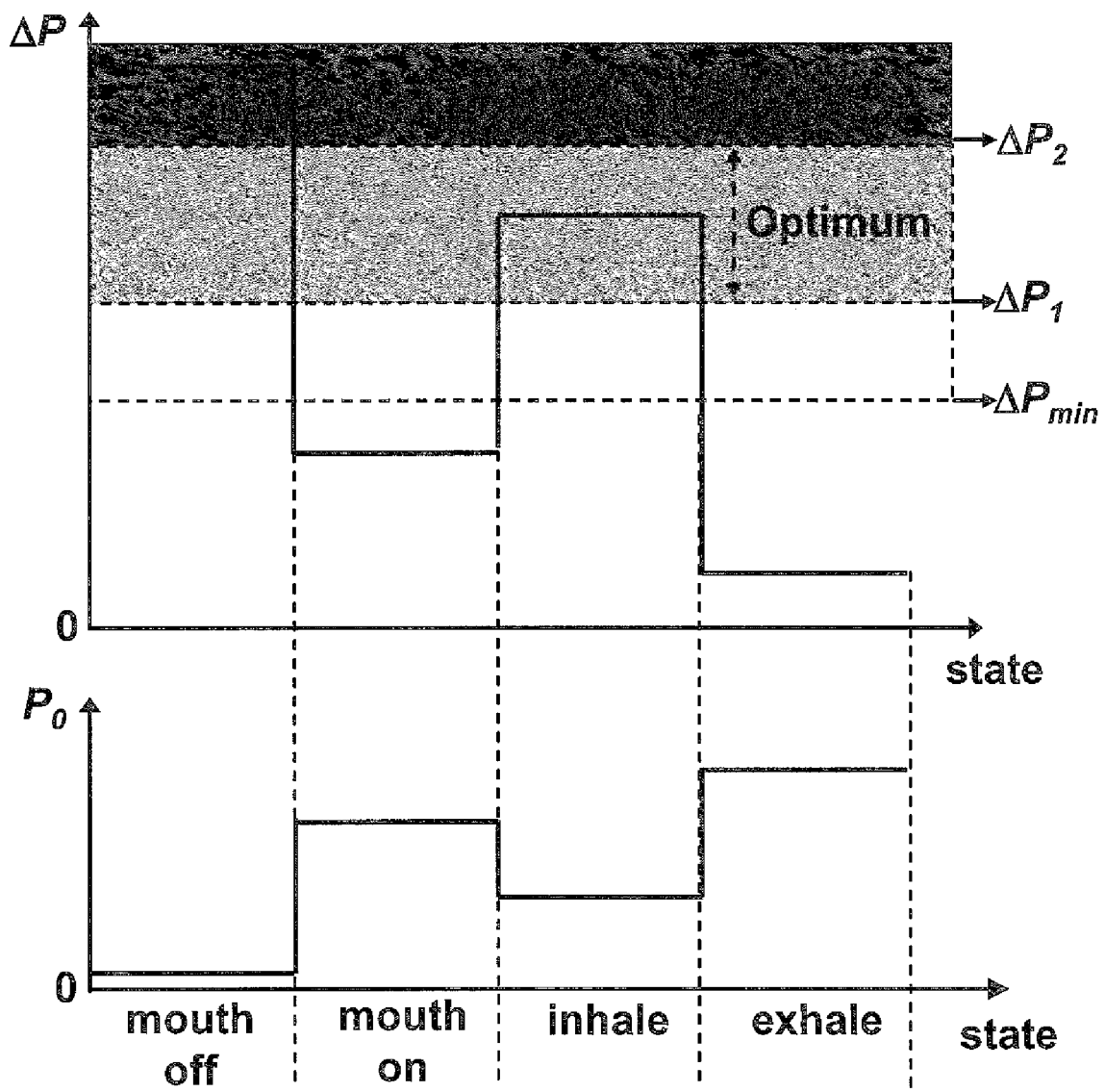
FIG. 11 illustrates the pressure and pressure differential measured in four possible states by a pressure sensor and pressure differential transducer respectively.

The novel aspects of this Respiratory Aerosol Control System (RACS) can be appreciated by observing the pressures and differential pressures in FIG. 11. Together, these uniquely define the patient's inhalation status. The pressure differential measured by the transducer 507 has 4 possible stages corresponding to 4 states: 1) mouth off, 2) mouth on, 3) inhale, and 4) exhale, which is schematically shown in the top row of FIG. 11. In the upper part of FIG. 11, $\Delta P_{min}$ corresponds to the minimum flow rate and the range between the $\Delta P_1$ and $\Delta P_2$ shows the optimum flow rate. When the pressure differential is greater than the $\Delta P_{min}$ and less than the .$\Delta P_1$, the yellow LED 603 is on. When the pressure differential is in the optimum range between the $\Delta P_1$ and $\Delta P_2$, the green LED 602 will be on. A pressure differential of greater than $\Delta P_2$ will turn the red LED 601 on. The output of the pressure ($P_O$) measured by pressure sensor 510 in the tube 502 is schematically shown in the bottom row of FIG. 11. When the patient's mouth is off the mouthpiece 503, the pressure $P_O$ is near zero. While the mouth is connected to the mouthpiece 503, and the user is not breathing either prior to inspiration or during a breath-hold, the pressure $P_O$ increases and turns the white LED 604 on. The pressure signal, $P_O$, responds in the opposite direction to that of the differential pressure 507 and thus a logic circuit using these parameters uniquely defines the breathing pattern of the patient on SUPRAER™. The logic circuits regulate both the flow indication lights and the fluid flow. Such a control system is unique to this respiratory aerosol control system, RAC.

Figure 12:
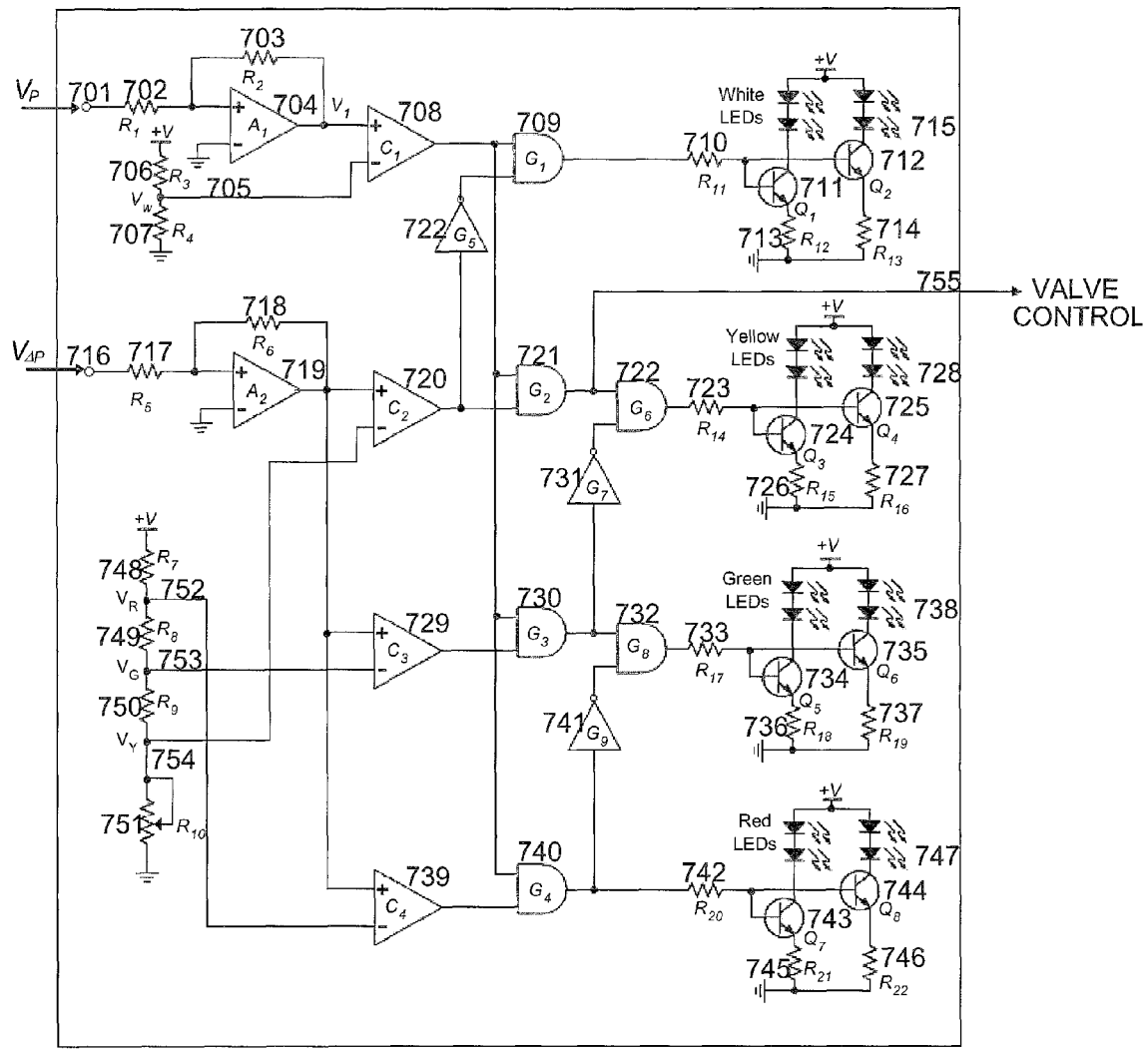
FIG. 12 is a schematic diagram of control circuitry for the respiratory aerosol control system.
Figure 13:
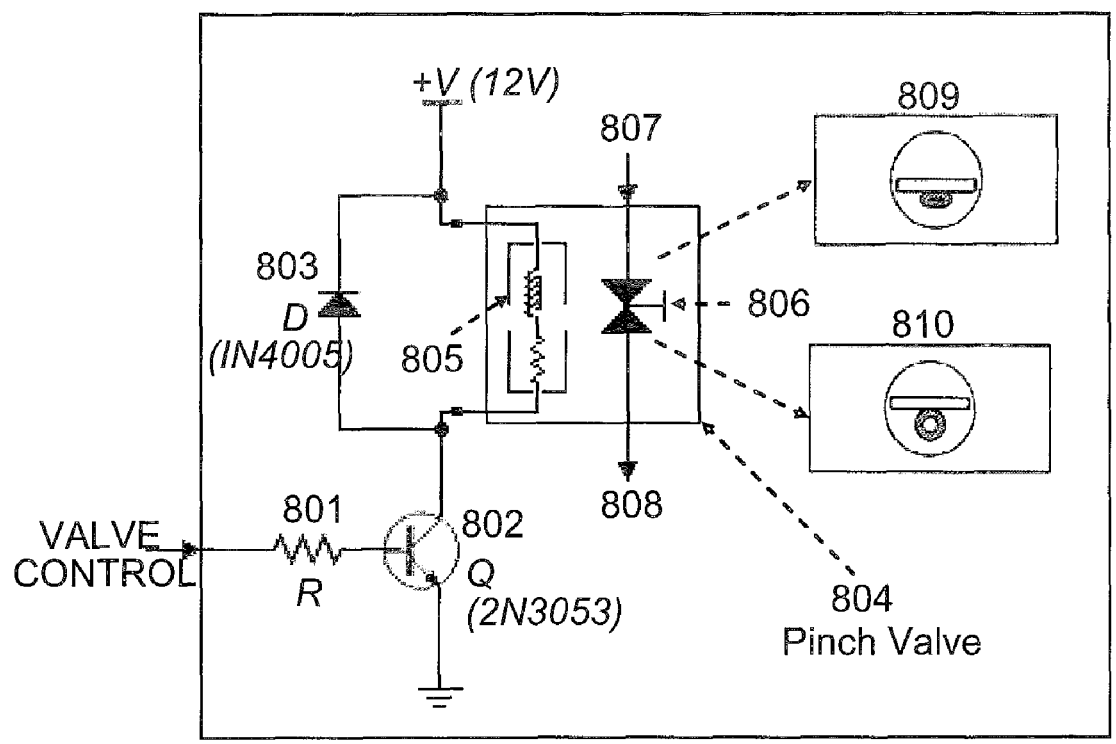
FIG. 13 is a schematic diagram of the fluid delivery controller.

The control circuitry of the respiratory aerosol control system is shown in FIG. 12. A low-power and low-cost amplifier in conjunction with a CMOS logic gate are used in a control circuit shown in FIG. 12. This circuitry uses 2 input signals, the output voltages of the pressure differential transducer 507 ($V_{\Delta P}$) and the pressure sensor 510 ($V_P$), to monitor the flow rate using the LED indicator FIG. 10B and operate a fluid delivery controller illustrated in (FIG. 13) for drug delivery during inspiration.

When the patient's mouth is not connected to the mouthpiece 503, FIG. 10A the air flow 505 passes through the tube 501 to the tube 502 and goes out 506 via the mouthpiece 503, while the check valve 513 remains in the closed state. An output voltage $V_P$ 701 of the pressure sensor 510 FIG. 10A is near zero. In reference to FIG. 12, the voltage $V_P$ is connected to the positive input of an amplifier 704 through a resistor 702, amplified by an amplifier 704, and applied to a positive input of a comparator 708. The output voltage of the amplifier 704 is compared with a reference voltage 705 that is set by a resistor "voltage divider" composed of 2 resistors 706, 707 and led to the negative input of the comparator 708. By setting the reference voltage 705 to be greater than the output voltage of the amplifier 704, the output of the comparator 708 is held to logic zero (ground). This logic zero is applied to one input pin of each of 4 two-input "AND" gates, 709, 721, 730, and 740, so the outputs of all 4 gates, 709, 722, 732, and 740, are logic 0, i.e. ($G_1$, $G_6$, $G_8$, $G_4$)=(0, 0, 0, 0). In this case, the gates 709, 722, 732, and 740 are unable to provide a current to the bases of 4 pairs of transistors (711 & 712, 724 & 725, 734 & 735, 743 & 744). These transistors are completely cut off with no collector current. All LEDs, 715, 728, 738, and 747, driven by the collector current of these transistors are turned off.

When a patient's mouth is connected to the mouthpiece 503, FIG. 10A, the pressure in the tubes 502 and 504 increases above the pressure threshold of a check valve 513. This valve 513 opens, so the airflow 505 passes through the valve 513 to ambient air. A voltage $V_P$ 701 increases to and remains at a positive value as shown in the lower part of FIG. 11. After amplification, the output voltage of the amplifier 704 is greater than the reference voltage 705, so the output of the comparator 708 changes from logic 0 to logic 1. The output voltage, $V_{\Delta P}$, 716 of the pressure differential transducer 507 is connected to the positive input of an amplifier 719 through a resistor 717, amplified by the amplifier 719 and applied to the positive inputs of 3 comparators, 720, 729, and 739. Three different reference voltages, 752, 753, and 754, which are determined by a resistor-network voltage divider composed of 4 resistors, 748, 749, 750, and 751, are connected to the 3 negative inputs of these 3 comparators, 720, 729, and 739, respectively. The 3 reference voltages satisfy $V_R > V_G > V_Y$, where the $V_Y$ 754 corresponds to the output voltage of the amplifier 719 at the pressure differential $\Delta P = \Delta P_{min}$, the $V_G$ 753 to the output voltage of the amplifier 719 at $\Delta P = \Delta P_i$, and the $V_R$ 752 to the output voltage of the amplifier 719 at $\Delta P = \Delta P_2$. In the mouth-on state, the pressure differential ($\Delta P$) measured by the pressure differential transducer 507, FIG. 10A is less than $\Delta P_{min}$ (as shown in the top row of FIG. 11). Again referring to FIG. 12, all 3 comparators, 720, 729, and 739, output a logical 0. With an input of logical 0, the output of the "NAND" gate 722 is logic 1. Both the inputs of an "AND" gate 709 are logic 1, so its output is logic 1. This provides a current through the resistor 710 to the bases of a pair of transistors 711 & 712. The transistors 711 & 712 are in the saturation condition with the maximum collector current. The white LED 715 composed of 4 white LEDs driven by the transistors 711 & 712 are lit, whereas the yellow 728, green 738 and red 747 LEDs remain turned-off because the outputs of "AND" gates; 722, 732, and 740, are held to logic 0.

When a pressure differential ($\Delta P$) 716 caused by an inhaled flow is in the range between the $\Delta P_{min}$ and $\Delta P_1$, the output voltage of the amplifier 719 is greater than the reference voltage 754 and less than both reference voltages 753 and 752. The output of the comparator 720 is logic 1, whereas the outputs of both comparators 729 and 739 are logic 0. The logic outputs of the 4 "AND" gates, 709, 722, 732, and 740, are ($G_1$, $G_6$, $G_8$, $G_4$)=(0, 1, 0, 0), so only the yellow LED 728 (comprising 4 yellow LEDs) is on, indicating insufficient inhalation flow. At this time, the others, white 715, green 738 and red 747 LEDs are turned off. When an inhaled flow is within the optimum range, the output voltage of the amplifier 719 is greater than both the reference voltages 754 and 753 and less than the reference voltage 752. The outputs of both comparators 720 and 729 are logic 1, whereas the output of the comparator 740 is logic 0. The logic outputs of the 4 "AND" gates, 709, 722, 732, and 740, are ($G_1$, $G_6$, $G_8$, $G_4$)= (0, 0, 1, 0). Only the green LED 738 (comprised of 4 green LEDs) is turned on to indicate an optimum inhalation flow and all others are off. When an inhaled flow causes a pressure differential greater than $\Delta P_2$, the output voltage of the amplifier 719 is greater than the reference voltages, 754 753, and 752. All 3 comparators, 720, 729, and 739, have an output held at logic 1. The logic outputs of the 4 "AND" gates, 709, 722, 732, and 740, are ($G_1$, $G_6$, $G_8$, $G_4$)=(0, 0, 0, 1) so that only the red LED 747 composed of 4 red LEDs is on, indicating that the inhalation flow rate is too high.

During the patient's exhalation, the one-way valve 512, FIG. 10A is closed and the pressure in the tube 504 increases to above the pressure threshold of the check valve 513. The valve 513 opens, so the patient's exhaled flow passes through the valve 513 to the outside. The pressure differential ($\Delta P$) 716 decreases to below $\Delta P_{min}$. The output voltage of the amplifier 719 is less than all 3 reference voltages, 754 753, and 752. All 3 comparators, 720, 729, and 739, output a logical 0. The logical outputs of the 4 "AND" gates, 709, 722, 732, and 740, are ($G_1$, $G_6$, $G_8$, $G_4$)=(1, 0, 0, 0). Only the white LED 715 is lit to indicate the exhalation.

Fluid delivery to the nebulizer is controlled by a normally closed, direct-current (DC) solenoid-operated 2-way pinch valve (Cole-Parmer Canada Inc.) (804 in FIG. 8). The breath-activated fluid delivery controller shown in FIG. 13, This controller is designed to deliver fluid carrying the active agent to the nebulizer throughout the inhalation. The control signal for the fluid delivery controller is from the output 755 of the "AND" gate 721 of FIG. 12.

During inhalation, when the pressure differential measured by the pressure differential transducer 507, FIG. 10A, is greater than the $\Delta P_{min}$ the output voltage of the amplifier 719, FIG. 11 is greater than the reference voltage 754, FIG. 11. The output of the comparator 720 is held to logic 1. As both inputs of the "AND" gate 721 are logic 1, the output 755 of the gate 721 is logic 1. This control signal 755 provides a current via a resistor 801, shown in FIG. 13, to the base of a transistor 802 (2N3053). The transistor 802 is completely open with the maximum collector current. While the collector current of the transistor passes through the wire coil wrapped on a solenoid electromagnet tube 805 FIG. 13 of the pinch valve 804, FIG. 8 and FIG. 13, the pinch valve 804 inverts from the normally closed state 809 to the opened state 810. Fluid goes from inlet 807 to outlet 808 of the pinch valve 804 and is delivered to the nebulizer for aerosolization. In the event that the patient's respiratory flow is insufficient to trigger the valve 804 for drug delivery, i.e., the output voltage of the amplifier 719 FIG. 12, is less than the reference voltage 754, the reference voltage 754 at the preset threshold can be reduced by adjusting the value of the variable resistor 751. As the output voltage of amplifier 719 is greater than the reference voltage 754, the valve 804 FIG. 8 and FIG. 13 can be triggered for drug delivery.

When the patient's mouth is off or during the exhalation, the output 755, FIG. 12 of the "AND" gate 721 is held to logic 0 which does not provide a current to the base of the transistor 802, FIG. 13. The transistor 802 is closed completely. The wire coil wrapped on the solenoid electromagnet tube 805 of the pinch valve 804 has no power supply and goes back to the normally closed state 809. No fluid is delivered.

EXAMPLES

To evaluate the APIS, five different orifice hole diameters, D=0.15 mm, 0.20 mm, 0.30 mm, 0.38 mm, and 0.5 mm; two capillary tube radii, $R_0$=0.28 mm, 0.55 mm; and two distances H, defined as the tube mouth to the orifice, H=1.0 mm and 1.5 mm; have been tested in a microfluidic flow aerosol generation unit.

Figure 14A:
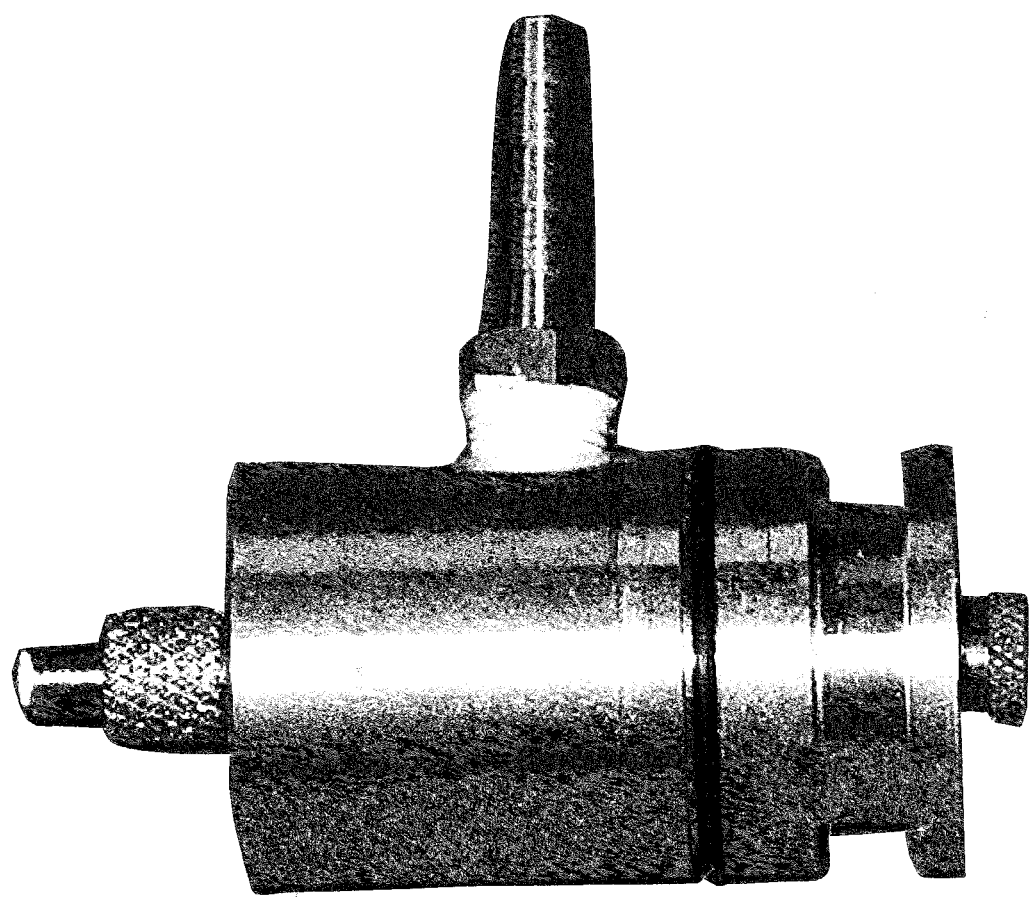
FIG. 14A is a photograph of the single orifice aerosol generator.
Figure 14B:
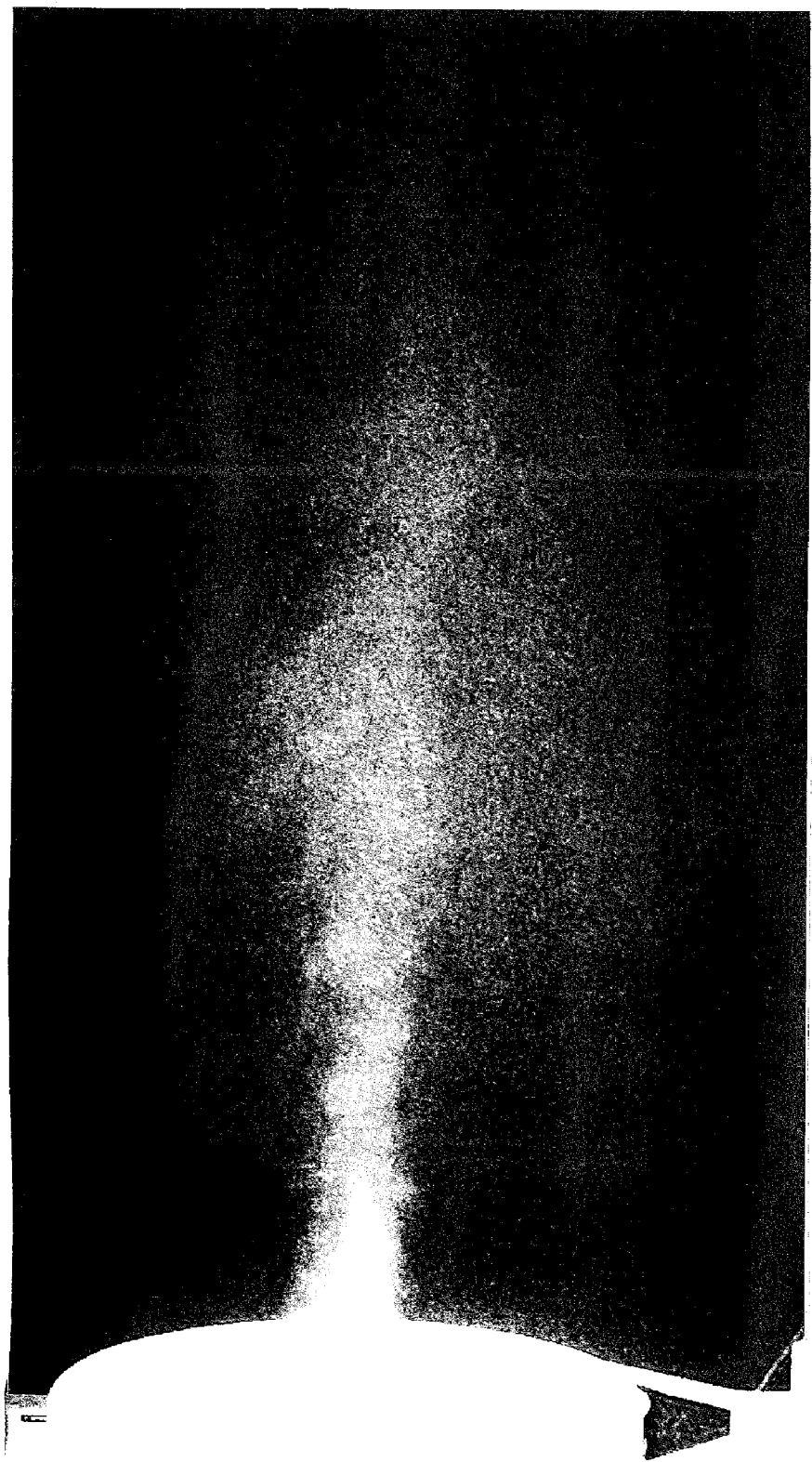
FIG. 14B is the spray pattern of the aerosol generated by the single orifice aerosol generator.
Figure 14C:
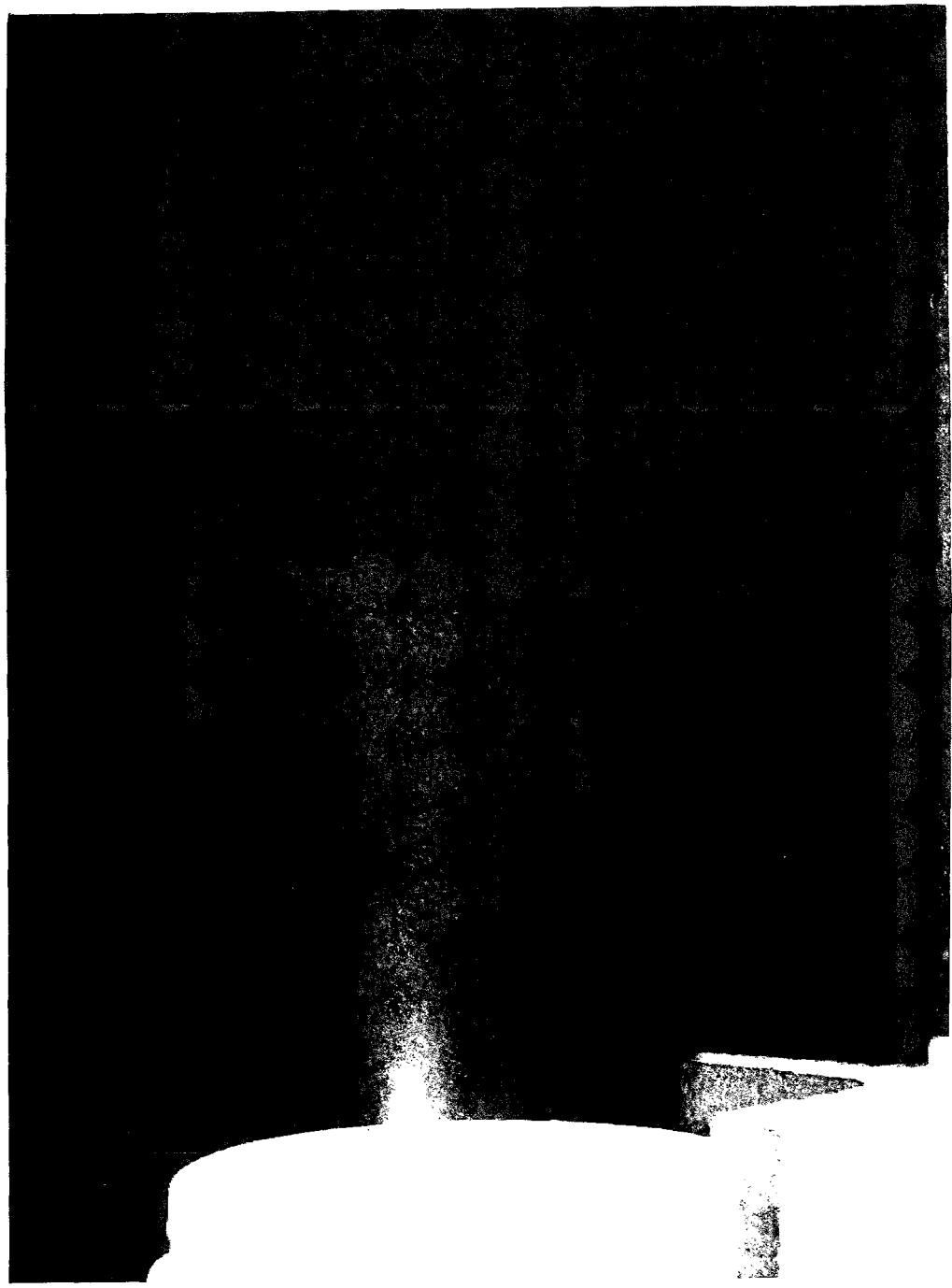
FIG. 14C is the arrest of the aerosol plume by a counter flow jet.

To evaluate the virtual impaction and arrest of the aerosol plume by the counter-flow air jet, photographs of the plume with and without the counter-flow air jet were taken. FIG. 14A is a photograph of the one orifice system. Fluid was injected into the capillary tubing using a syringe pump (Model 600-900VDCM, Harvard Apparatus). Compressed air was provided (Jun Air compressor). Using 1.1 mm diameter capillary tubing, 0.5 mm (0.02") diameter orifice, and 1.0 mm distance from the open end of the capillary tubing to the orifice, the spray pattern of the aerosol generated by the single-orifice aerosol generator was recorded using a Kodak digital camera (FIG. 14B). The arrest of the aerosol plume by a counter flow jet is shown in FIG. 14C.

A fabricated 5-orifice generation system was used in one embodiment, generating an aerosol plume. The central orifice was used for air supply, and other four orifices were used for the aerosol generation in the experiments. A multi-syringe pump (A Harvard Apparatus Model 2 55-5920) was used to provide identical fluid flow rate to each aerosol generation orifice. The multi-orifice aerosol generator can generate aerosol at fluid flow rates of up to 15 ml/min. The mass median aerodynamic diameters of the droplets generated and the particles are well within the design parameters of the system.

The effectiveness of the processes engaged to rapidly evaporate the large particle aerosols within a small volume aging chamber were evaluated. After optimization with the 12 inch aging chamber, we were able to completely evaporate the aqueous droplets in less than 6 inches when the fluid flow was 4 ml/min. Thus, further experiments were carried out using the 6 inch aging chamber. The mean axial velocity of 300 l/min air in the 3.0 inch inner diameter evaporation chamber is 1 m/sec. The heated annular swirling dilution air jet can be adjusted with consideration of the solution particle size and the dose desired.

To increase the droplet evaporation rate, the temperature of the swirling annular air jet and counter-flow air jet were maintained at 60° C. using two mechanisms. First, four cartridge heaters (2 inches long, 0.25 inch wide) were embedded in the atomizer aluminum body (see FIG. 3A). The output of each heater was adjusted using an OMEGA CN8500 temperature controller to maintain the output aerosol at 37° C. Three OMEGA J TYPE fine thermocouples were used to monitor the temperatures of the heaters, aerosol at the exit of the aerosol generator, and aerosol at the outlet of the APIS. The temperature of the heater was 87° C. with room temperature air passing through it at about 300 l/min and a fluid flow rate of 3 ml/min. The fluid flowing through capillary tubes inside the atomizer body was also warmed. Second, a 300 W infrared radiant lamp was used to transfer energy into the chamber through the Pyrex glass walls to increase evaporation rate.

After optimization with the 12-inch aging chamber, we were able to completely evaporate the aqueous droplets in less than 6" when the fluid flow rate was 4 ml/min. Thus, a 3 inch inner diameter 6 inch long Pyrex glass tube was used as an aging chamber.

To evaluate the performance of the APIS, the output aerosol was characterized using an aqueous saline solution (NaCl). An 8% saline solution containing 0.05% fluoroscein was injected into the aerosol generator at 1.about.5 ml per minute. The fluid in the aerosol was evaporated, producing an aerosol of crystalline salt particles. The particle size distribution of the residual salt crystals was determined using a five-stage Marple-Miller Cascade Impactor (Model #: 150, MSP Corporation) operated at a flow rate of 30 l/min. The cut-off diameters of 1, 2, 3, 4 and 5 stages are 9.9 µm, 5 µm, 2.5 µm, 1.13 µm, 0.63 µm, respectively. A 47 mm membrane filter paper with 0.45 µm pore size was used to collect particles smaller than 0.63 µm at the end-stage of the cascade impactor. The NaCl containing fluoroescein collected in each stage of the cascade impactor and the filter paper was washed with 3 ml phosphate buffer solution with pH=7.4. The fluorescein concentration was measured at 490 nm using an LKB spectrophotometer (Model ULTROSPEC II). Thus, the relative mass of NaCl collected at each stage of the cascade impactor and the filter paper was determined and the cumulative mass deposited on each stage of the impactor was expressed as percent of the total mass deposited. Experiments were carried out using a 6 inch long Pyrex glass tube as the aging chamber. The mean axial velocity of 300 l/min air in the 3.0 inch inner diameter evaporation chamber was 1 m/sec.

The distribution of particles generated by the single-orifice aerosol generator at fluid flow rate Q=3 ml/min and various compressed air pressures of 8-40 psi is shown in Table 3. An orifice diameter of D=0.5 mm, capillary tube diameter of $2R_0$=1.1 mm, distance from the tube mouth to the orifice H=1.0 mm, input air flow $Q_{air\_in}$=300 l/min and output air flow $Q_{air\_out}$=30 l/min were used. The residual NaCl crystals had a mass median aerodynamic diameter of 2.5 µm with a geometric standard deviation $\sigma_g$ of 1.58 using jet aerosolization air pressures of 40 psi. 86% of the particles were smaller than 5 µm, and 72% of particles were in the range 1.13 µm to 5 µm. As seen from Table 3, the particle distribution is not strongly dependent on the compressed air pressure in the range 8 psi to 40 psi. The size distribution of the droplets at the moment of formation was calculated using $d_d = d_p/X^{1/3}$, where X is volume concentration of saline solution, $d_d$ and $d_p$ are droplet and particle diameters, respectively.

TABLE 3

Effects of air pressure on particle display

| Compressed air pressure Psi | Particle Mass Median aerodynamic diameter (µm) | Droplet Mass Median aerodynamic diameter (µm) | Geometric standard deviation $\sigma_g$ |
|---|---|---|---|
| 40 | 2.5 | 12.9 | 1.58 |
| 30 | 2.7 | 13.9 | 1.68 |
| 20 | 2.4 | 12.4 | 1.65 |
| 15 | 2.7 | 13.9 | 1.65 |
| 10 | 2.8 | 14.5 | 1.64 |
| 8 | 2.8 | 14.5 | 1.68 |

Thus, the mass median aerodynamic diameters of the droplets generated and the particles are well within the design parameters of the system. The liquid flow rate does not greatly affect the mass median aerodynamic diameters of the particles generated, as shown in Table 4.

TABLE 4

Effects of Fluid Flow on Particle Distribution

| Liquid flow rate, Ml/min | Particle mass median aerodynamic diameter, µm | Droplet mass median aerodynamic diameter, µm | Geometric standard deviation $\sigma_g$ |
|---|---|---|---|
| 5 | 2.5 | 12.9 | 1.57 |
| 4 | 2.5 | 12.9 | 1.56 |
| 3 | 2.5 | 12.9 | 1.60 |

The particle distribution generated by the multi-orifice aerosol generator operated at a compressed air pressure of 35 psi with a fluid flow rate of Q=3 ml/min and 4 ml/min were also determined using a five stage Marple-Miller Cascade Impactor, and is shown in Table 5. An orifice with a diameter D=0.3 mm, the capillary tube with a diameter of $2R_0$=0.56 mm, the distance from open end of the tube mouth to the orifice H=0.5 mm, and input air flow $Q_{air\_in}$=300 l/min and output air flow $Q_{air\_out}$=30 l/min were used,

TABLE 5

Distribution of particles generated by 4-orifice aerosol generator

| Liquid flow rate, Ml/min | Particle mass median aerodynamic diameter, μm | Droplet mass median aerodynamic diameter, μm | Geometric standard deviation, $\sigma_g$ |
|---|---|---|---|
| 3 | 2.3 | 11.9 | 1.59 |
| 4 | 2.5 | 12.9 | 1.70 |

The concentration factor, the ratio of the output aerosol concentration to the input aerosol concentration, was determined using saline solution. When coaxial counterflow air jet nozzle with a diameter of 1.8 mm, the counterflow jet flowrate $Q_{counter\_flow}$=5 l/min and air pressure of 10 psi were used, the particle size distributions and the aerosol concentration factors are summarized in Table 6. The distribution of the particles in the APIS output aerosol was measured at a fluid flow rate of 3.0 ml/min and the compressed air jet pressures of 30 psi, 35 psi and 40 psi. The particles have a mass median aerodynamic diameter of 2.5 μm with a geometric standard deviation of 1.58 at the compressed air jet pressure of 40 psi. When the compressed air jet pressure was decreased to 30 psi, the particle mass median aerodynamic diameter was 2.7 μm with a geometric standard deviation of 1.60. The efficiency of a single stage concentrator, defined as a ratio of mass of the output drug to mass of the input drug, is around 63% at the output with an input around 10%.

The embodiment of this part of the invention is solely for purposes of illustration and should not be construed as limiting the scope of the present invention.

TABLE 6

Performance of Concentrator

| Compressed air Pressure, psi | Particle mass median aerodynamic diameter (μm) | Geometric Standard deviation | Concentration factor |
|---|---|---|---|
| 40 | 2.5 | 1.58 | 6.3 |
| 35 | 2.5 | 1.60 | 6.4 |
| 30 | 2.7 | 1.68 | 6.3 |

The concentration factor shown is well within the design parameters of the invention, and can be adjusted according to the desired performance by small design changes.

Evaluation of the Performance of APIS (1) The counter-flow was able to arrest the aerosol plume comprising an aerosol of 2.5 to 2.8 μm mass median aerodynamic diameter.

(2) The mass median aerodynamic diameters of the liquid droplets generated and the residual particles are well within the design parameters of the system.

(3) The aerosol evaporation was complete in the confined volume. Initial large droplets completely evaporated within a 3 inch inner diameter and 6 inch long aging chamber when fluid flow rate=4 ml/min and air flow rate=300 l/min.

(4) About 64% of the NaCl was transported from the syringe (drug container) to the output of the APIS.

(5) Concentration factors of over 6 were easy to obtain.

The objects of this invention can be achieved by many techniques and methods known to persons who are skilled in this field. To those skilled and knowledgeable in the arts to which the present invention pertains, many widely differing embodiments will be suggested by the foregoing without departing from the intent and scope of the present invention. The descriptions and disclosures herein are intended solely for purposes of illustration and should not be construed as limiting the scope of the present invention as described in the appended claims.

What is claimed is:

1. A method for producing concentrated aerosols in a compact device suitable for inhalation therapy, said device comprising
   an aerosol generator;
   an aerosol evaporator engaged by and in communication with the aerosol generator; said aerosol evaporator having a chamber with a cylindrical chamber wall and a central axis;
   an aerosol concentrator engaged by and in communication with the aerosol evaporator; and
   an aerosol flow regulator that is connected to the aerosol concentrator, said method comprising:
   generating by means of the aerosol generator a large liquid aerosol flow and directing the large liquid aerosol flow into a first direction of flow extending along the central axis;
   reducing the velocity of the large liquid aerosol flow by directing a counterflow air jet into a second direction of flow that is opposed to the first direction of flow against the large liquid aerosol flow;
   generating a sheath air flow for minimizing aerosol deposition on the chamber;
   mixing the sheath air flow with the large liquid aerosol flow and counterflow for augmenting evaporation of the large liquid aerosol;
   generating at least one of convective heat and radiative heat and transferring this heat into the chamber, evaporating liquid contained in the large liquid aerosol by dry air mixing to form a flow comprising a dry aerosol powder having a particle size between 1 μm and 10 μm;
   concentrating the dry aerosol powder by virtual impaction removing most of the air and unwanted vapor as a major fraction from a remaining small fraction containing air, vapor and dry aerosol powder;
   providing stable dry particles of the dry aerosol powder containing up to 100% active agents;
   regulating aerosol production during inhalation using a respiratory aerosol control system; and
   providing flow derived visible indicators.

2. The method of claim 1, wherein droplet size in the liquid aerosol produced is in the range 10-50 μm in diameter.

3. The method of claim 1, wherein initial generation of large droplets is suitable for the respiratory delivery of large molecules in respirable particles.

4. The method of claim 1, wherein a two-stage aerosol concentrator and evaporator is used.

5. The method of claim 1, wherein the aerosol exiting the system has a flow rate in the range of 10 l/min to 90 l/min.

6. The method of claim 1, wherein the large liquid aerosol comprises water as a liquid solvent.

7. The method of claim 1, wherein the large liquid aerosol comprises one of alcohol, hydrofluoroalkane, chlorofluorocarbon or carbon dioxide as a liquid solvent.

8. The method of claim 1, wherein the liquid in the aerosol has a vapor pressure equal to or greater than water.

9. The method of claim 1, wherein the liquid aerosol is generated by a micro-fluidic focused-flow monodisperse spray generation technique.

10. The method of claim 1, wherein the liquid aerosol is generated by a jet.

11. The method of claim 1, wherein the device is portable.

12. The method of claim 1, wherein the aerosol is generated by at least one of continuously and on demand by a patient.

13. A method for producing concentrated aerosols in a compact device suitable for inhalation therapy, said device comprising
    an aerosol generator;
    an aerosol evaporator engaged by and in communication with the aerosol generator; said aerosol evaporator having a chamber with a cylindrical chamber wall and a central axis;
    an aerosol concentrator engaged by and in communication with the aerosol evaporator; and
    an aerosol flow regulator that is connected to the aerosol concentrator, said method comprising:
    generating by means of the aerosol generator a large liquid aerosol flow and directing the large liquid aerosol flow into a first direction of flow extending along the central axis;
    reducing the velocity of the large liquid aerosol flow by directing a counterflow air jet into a second direction of flow that is opposed to the first direction of flow against the large liquid aerosol flow;
    generating a sheath air flow for minimizing aerosol deposition on the chamber;
    mixing the sheath air flow with the large liquid aerosol flow and counterflow for augmenting evaporation of the large liquid aerosol;
    generating at least one of convective heat and radiative heat and transferring this heat into the chamber, evaporating liquid contained in the large liquid aerosol by dry air mixing to form a flow comprising a dry aerosol powder having a particle size between 1 µm and 10 µm;
    concentrating the dry aerosol powder by virtual impaction removing most of the air and unwanted vapor as a major fraction from a remaining small fraction containing air, vapor and dry aerosol powder;
    providing stable dry particles of the dry aerosol powder containing up to 100% active agents.

14. A system for producing concentrated aerosols in a compact device suitable for inhalation therapy, said system comprising the elements of:
    a chamber with a cylindrical chamber wall and a central axis extending into a first direction of flow;
    means generating a sheath of dry air flow for minimizing aerosol deposition on the chamber;
    an aerosol generator having at least one orifice adapted to eject a large liquid aerosol flow into the chamber along the central axis in the first direction of flow;
    an aerosol evaporator engaged by and in communication with the aerosol generator;
    a coaxial counterflow air jet nozzle reducing the velocity of the aerosol by directing a counterflow air jet into a second direction of flow that is opposed to the first direction of flow and therefore directed against the aerosol;
    at least one of a convective or radiative heat transfer device heating at least one of dry air flowing into the chamber and being within said chamber;
    an aerosol concentrator engaged by and in communication with the aerosol evaporator, said concentrator being adapted to remove most of the air and unwanted vapor as a major fraction from a remaining small fraction containing air, vapor and dry aerosol powder; and
    an aerosol flow regulator that is connected to the aerosol concentrator.

15. The system of claim 14, wherein the aerosol generator comprises either a first single orifice or a first multiple orifice system and the large liquid aerosol injected through the first orifice or first multiple orifice system is sheathed in pressurized air and fed through a second orifice such that a stable microjet of liquid emerges to form an aerosol plume.

16. The system of claim 14, wherein the aerosol generator comprises a system in which liquid aerosol is generated by a jet nebulizer.

17. The system of claim 14, wherein the aerosol evaporator comprises means for augmenting evaporation of the liquid aerosol by at least one of high velocity dry air-aerosol mixing, countercurrent virtual impaction, swirling annular mixing and infrared radiation.

18. The system of claim 14, wherein the aerosol concentrator utilizes virtual impaction.

19. The system of claim 14, wherein the aerosol flow regulator comprises devices in which regulation of the breathing pattern and inspiratory flow are achieved using one-way valves, pressure transducers, electronic control circuitry and output indicator lights.

20. The system of claim 14, wherein the system is adapted to be used as an aerosol processing and inhalation system for clinic applications incorporating a two-stage aerosol concentrator.

21. The system of claim 20, wherein the aerosol processing and inhalation system for clinical applications are of dimensions to produce a hand-held aerosol delivery device.

22. The system of claim 20, wherein the aerosol processing and inhalation system for clinic applications incorporates a disposable drug cartridge.

23. The system of claim 20, wherein the aerosol processing and inhalation system for clinic applications provides identical total dose rates for each and every treatment.

24. The system of claim 20, wherein the aerosol processing and inhalation system for clinic applications features a disposable drug cartridge that can be easily replaced.

25. The system of claim 20, wherein the aerosol processing and inhalation system for clinic applications provides a constant fluid flow rate.

26. The system of claim 20, wherein the aerosol processing and inhalation system for clinic applications provides a combination of a LED and photoelectric cells to provide the patient feedback for the correct breathing pattern.

27. The system of claim 20, wherein the aerosol processing and inhalation system for clinic applications incorporates a respiratory aerosol control system.

28. The system of claim 20, wherein the aerosol processing and inhalation system for clinic applications controls a pinch one way valve for drug fluid automatic delivery.

29. The system of claim 20, wherein the aerosol processing and inhalation system for clinic applications enables patients to inhale aerosol drug while they breathing continuously through the aerosol processing and inhalation system.

30. The system of claim 20, wherein the aerosol processing and inhalation system for clinic applications can monitor respiratory flow rate for optimization of breathing pattern.

31. The system of claim 20, wherein the aerosol processing and inhalation system for clinic applications can provide an alarm signal when a treatment is over.

32. The system of claim 14 comprising a respiratory aerosol control system utilizing both a pressure transducer together with differential pressure transducer across a flow element and a resistive one way valve in which the output of these transducers logically and uniquely define the patients breathing status.

33. The system of claim 32 wherein the flow element in the respiratory control system is a Venturi flow element.

34. The system of claim 14, wherein the aerosol generator comprises a system in which liquid aerosol is generated by a focused flow monodisperse aerosol generation technique.

35. A system for producing concentrated aerosols in a compact device, said system comprising the elements of:
 a chamber with a cylindrical chamber wall and a central axis extending into a first direction of flow;
 means generating a sheath of dry air flow for minimizing aerosol deposition on the chamber;
 an aerosol generator having at least one orifice adapted to eject a large liquid aerosol flow into the chamber along the central axis in the first direction of flow;
 an aerosol evaporator engaged by and in communication with the aerosol generator;
 a coaxial counterflow air jet nozzle reducing the velocity of the aerosol by directing a counterflow air jet into a second direction of flow that is opposed to the first direction of flow and therefore directed against the aerosol;
 at least one of a convective or radiative heat transfer device heating at least one of dry air flowing into the chamber and being within said chamber;
 an aerosol concentrator engaged by and in communication with the aerosol evaporator, said concentrator being adapted to remove most of the air and unwanted vapor as a major fraction from a remaining small fraction containing air, vapor and dry aerosol powder.

* * * * *